US 9,956,281 B2

(12) United States Patent
Ryan et al.

(10) Patent No.: US 9,956,281 B2
(45) Date of Patent: May 1, 2018

(54) INACTIVATED VIRUS COMPOSITIONS AND METHODS OF PREPARING SUCH COMPOSITIONS

(75) Inventors: Wayne L. Ryan, Omaha, NE (US); James A Grunkemeyer, Omaha, NE (US)

(73) Assignee: STRECK, INC., LaVista, NE (US)

( * ) Notice: Subject to any disclaimer, the term of this patent is extended or adjusted under 35 U.S.C. 154(b) by 151 days.

(21) Appl. No.: 14/112,263

(22) PCT Filed: May 3, 2012

(86) PCT No.: PCT/US2012/036304
§ 371 (c)(1),
(2), (4) Date: Oct. 17, 2013

(87) PCT Pub. No.: WO2012/151391
PCT Pub. Date: Nov. 8, 2012

(65) Prior Publication Data
US 2014/0044752 A1 Feb. 13, 2014

Related U.S. Application Data

(60) Provisional application No. 61/482,367, filed on May 4, 2011.

(51) Int. Cl.
| A61K 39/00 | (2006.01) |
| A61K 39/145 | (2006.01) |
| C07K 14/005 | (2006.01) |
| C07K 14/11 | (2006.01) |
| A61K 39/12 | (2006.01) |
| A61K 39/275 | (2006.01) |
| C12N 7/00 | (2006.01) |

(52) U.S. Cl.
CPC ............ *A61K 39/275* (2013.01); *A61K 39/12* (2013.01); *C12N 7/00* (2013.01); *A61K 2039/5252* (2013.01); *C12N 2760/16134* (2013.01); *C12N 2760/16163* (2013.01)

(58) Field of Classification Search
CPC ............ A61K 2039/5252; A61K 31/35; A61K 36/00; A61K 39/12; A61K 39/275
See application file for complete search history.

(56) References Cited

U.S. PATENT DOCUMENTS

| 3,867,521 A | 2/1975 | Miskel et al. |
| 3,885,011 A | 5/1975 | Renoux et al. |
| 4,053,583 A | 10/1977 | Gits et al. |
| 4,235,876 A | 11/1980 | Gits et al. |
| 4,515,890 A | 5/1985 | Manderino et al. |
| 4,675,159 A | 6/1987 | Al-Sioufi |
| 5,152,981 A | 10/1992 | Rones et al. |
| 5,162,112 A | 11/1992 | Oxford et al. |
| 5,196,182 A | 3/1993 | Ryan |
| 5,213,765 A | 5/1993 | Kasai et al. |
| 5,250,438 A | 10/1993 | Ryan |
| 5,257,633 A | 11/1993 | Vogler et al. |
| 5,260,048 A | 11/1993 | Ryan |
| 5,427,791 A | 6/1995 | Ahmad et al. |
| 5,447,842 A | 9/1995 | Simons |
| 5,457,024 A | 10/1995 | Goldbard |
| 5,459,073 A | 10/1995 | Ryan |
| 5,459,253 A | 10/1995 | Wolin et al. |
| 5,460,797 A | 10/1995 | Ryan |
| 5,501,954 A | 3/1996 | Mahr |
| 5,614,391 A | 3/1997 | Franciskvoich et al. |
| 5,618,664 A | 4/1997 | Kiessling |
| 5,629,147 A | 5/1997 | Asgari |
| 5,731,156 A | 3/1998 | Golbus |
| 5,733,556 A | 3/1998 | Schrier et al. |
| 5,783,093 A | 7/1998 | Holme |
| 5,811,099 A | 9/1998 | Ryan |
| 5,817,519 A | 10/1998 | Zelmanovic et al. |
| 5,849,517 A | 12/1998 | Ryan |
| 5,858,699 A | 1/1999 | Granger et al. |
| 5,861,253 A | 1/1999 | Asgari et al. |
| 5,906,744 A | 5/1999 | Carroll et al. |
| 5,962,234 A | 10/1999 | Golbus |
| 5,977,153 A | 11/1999 | Camiener |
| 5,985,572 A | 11/1999 | Macfarlane |
| 6,013,240 A | 1/2000 | Behr et al. |
| 6,030,767 A | 2/2000 | Wagner |
| 6,043,032 A | 3/2000 | Yamagishi et al. |

(Continued)

FOREIGN PATENT DOCUMENTS

| CA | 2406463 | 1/2001 |
| DE | 19928820 | 12/2000 |
| EP | 1031626 A1 | 8/2000 |
| EP | 1217372 A1 | 6/2002 |
| EP | 1816461 A1 | 8/2007 |
| EP | 1889921 A2 | 2/2008 |
| EP | 1425294 B1 | 7/2008 |
| EP | 2228453 A1 | 9/2010 |
| EP | 2216416 | 11/2010 |
| EP | 2411808 B1 | 11/2015 |
| WO | 93/05650 | 4/1993 |
| WO | 94/02646 | 2/1994 |
| WO | 95/26417 | 10/1995 |
| WO | 98/02528 A1 | 1/1998 |
| WO | 98/02740 A1 | 1/1998 |

(Continued)

OTHER PUBLICATIONS

International Search Report and Written Opinion International Application No. PCT/US2012/036304 dated Nov. 21, 2012.

(Continued)

*Primary Examiner* — Barry A Chestnut
(74) *Attorney, Agent, or Firm* — The Dobrusin Law Firm, P.C.

(57) ABSTRACT

The present invention is directed at a composition comprising a live swine flu virus having an infectious component and a plurality of surface antigens in contact with a formaldehyde donor agent having a molecular weight that is less than about 400 g/mol. Preferably, the formaldehyde donor agent is selected from a non-crosslinking chemical fixative that contains urea.

15 Claims, 14 Drawing Sheets

(56) References Cited

U.S. PATENT DOCUMENTS

| | | |
|---|---|---|
| 6,077,235 A | 6/2000 | Serpentino et al. |
| 6,136,321 A | 10/2000 | Barrett et al. |
| 6,159,472 A | 12/2000 | Hein |
| 6,168,922 B1 | 1/2001 | Harvey et al. |
| 6,190,609 B1 | 2/2001 | Chapman |
| 6,197,539 B1 | 3/2001 | Granger |
| 6,197,540 B1 | 3/2001 | Granger |
| 6,210,889 B1 | 4/2001 | Drouin et al. |
| 6,218,531 B1 | 4/2001 | Ekenberg |
| 6,251,638 B1 | 6/2001 | Umansky et al. |
| 6,258,540 B1 | 7/2001 | Lo et al. |
| 6,287,820 B1 | 9/2001 | Umansky et al. |
| 6,337,189 B1 | 1/2002 | Ryan |
| 6,344,354 B1 | 2/2002 | Webster et al. |
| 6,365,362 B1 | 4/2002 | Terstappen et al. |
| 6,527,957 B1 | 3/2003 | Deniega |
| 6,551,267 B1 | 4/2003 | Cohen et al. |
| 6,579,672 B1 | 6/2003 | Granger |
| 6,602,718 B1 | 8/2003 | Augello et al. |
| 6,617,170 B2 | 9/2003 | Augello et al. |
| 6,617,180 B1 | 9/2003 | Wang |
| 6,623,983 B1 | 9/2003 | Terstappen et al. |
| 6,630,301 B1 | 10/2003 | Gocke et al. |
| 6,645,731 B2 | 11/2003 | Terstappen et al. |
| 6,653,062 B1 | 11/2003 | DePablo et al. |
| 6,664,056 B2 | 12/2003 | Lo et al. |
| 6,759,217 B2 | 7/2004 | Kopreski et al. |
| 6,821,789 B2 | 11/2004 | Augello et al. |
| 6,884,573 B2 | 4/2005 | Fischer |
| 6,916,634 B2 | 7/2005 | Kopreski |
| 6,939,671 B2 | 9/2005 | Kopreski |
| 6,994,790 B2 | 2/2006 | Corbin |
| 7,044,941 B2 | 5/2006 | Mathias |
| 7,208,275 B2 | 4/2007 | Gocke et al. |
| 7,252,984 B2 | 8/2007 | Mast et al. |
| 7,267,980 B1 | 9/2007 | Mortari et al. |
| 7,282,371 B2 | 10/2007 | Helftenbein |
| 7,288,380 B1 | 10/2007 | Gocke et al. |
| 7,314,715 B2 | 1/2008 | Cochran et al. |
| 7,332,169 B2 | 2/2008 | Peeters et al. |
| 7,332,277 B2 | 2/2008 | Dhallan |
| 7,332,288 B2 | 2/2008 | Terstappen et al. |
| 7,358,039 B2 | 4/2008 | Fischer |
| 7,390,663 B2 | 6/2008 | Ryan et al. |
| 7,419,832 B2 | 9/2008 | Hunsley |
| 7,442,506 B2 | 10/2008 | Dhallan |
| 7,445,901 B2 | 11/2008 | Kudlicki et al. |
| 7,569,350 B2 | 8/2009 | Gocke et al. |
| 7,651,838 B2 | 1/2010 | Paterlini-Brechot |
| 2001/0018192 A1 | 8/2001 | Terstappen et al. |
| 2001/0051341 A1 | 12/2001 | Lo et al. |
| 2002/0045196 A1 | 4/2002 | Mahoney et al. |
| 2002/0086346 A1 | 7/2002 | Ryan |
| 2002/0119503 A1 | 8/2002 | Ryan et al. |
| 2003/0026813 A1 | 2/2003 | Gallili et al. |
| 2003/0232377 A1 | 12/2003 | Thomas |
| 2004/0038424 A1 | 2/2004 | Maples |
| 2004/0137417 A1 | 7/2004 | Ryan |
| 2005/0029559 A9 | 2/2005 | Ahn et al. |
| 2005/0049793 A1 | 3/2005 | Paterlini-Brechot |
| 2005/0181353 A1 | 8/2005 | Rao et al. |
| 2005/0181463 A1 | 8/2005 | Rao et al. |
| 2005/0277204 A1 | 12/2005 | Hollis et al. |
| 2006/0008807 A1 | 1/2006 | O'Hara et al. |
| 2006/0105372 A1 | 5/2006 | Bair et al. |
| 2006/0147468 A1 | 7/2006 | Barrett |
| 2006/0194192 A1 | 8/2006 | Rao et al. |
| 2006/0210429 A1 | 9/2006 | Hunsley et al. |
| 2007/0077559 A1 | 4/2007 | Bamat et al. |
| 2007/0082012 A1 | 4/2007 | Shields |
| 2007/0111233 A1 | 5/2007 | Bianchi et al. |
| 2007/0134658 A1 | 6/2007 | Bohmer |
| 2007/0178115 A1 | 8/2007 | Tang et al. |
| 2007/0178478 A1 | 8/2007 | Dhallan |
| 2007/0202525 A1 | 8/2007 | Quake et al. |
| 2007/0251337 A1 | 11/2007 | Reed et al. |
| 2008/0020390 A1 | 1/2008 | Mitchell et al. |
| 2008/0057502 A1 | 3/2008 | Kopreski |
| 2008/0081689 A1 | 4/2008 | Seelig et al. |
| 2008/0096217 A1 | 4/2008 | Kopreski |
| 2008/0102470 A1 | 5/2008 | Dawson |
| 2008/0108071 A1 | 5/2008 | Thompson |
| 2008/0119645 A1 | 5/2008 | Griffey et al. |
| 2008/0261292 A1 | 10/2008 | Kopreski |
| 2008/0318801 A1 | 12/2008 | Leung et al. |
| 2009/0081678 A1 | 3/2009 | Ryan et al. |
| 2010/0167271 A1 | 7/2010 | Ryan |
| 2010/0184069 A1 | 7/2010 | Fernando et al. |
| 2010/0209930 A1 | 8/2010 | Fernando |
| 2010/0216153 A1 | 8/2010 | Lapidus et al. |
| 2010/0317107 A1 | 12/2010 | Ryan |
| 2011/0027771 A1 | 2/2011 | Deng |
| 2011/0110975 A1* | 5/2011 | Grunkemeyer ........ A61K 39/17 424/204.1 |
| 2011/0111410 A1 | 5/2011 | Ryan et al. |
| 2013/0034860 A1 | 2/2013 | Fernando |
| 2014/0054508 A1 | 2/2014 | Fernando |
| 2015/0301037 A1 | 10/2015 | Tsinberg et al. |
| 2016/0143268 A1 | 5/2016 | Ryan |

FOREIGN PATENT DOCUMENTS

| | | |
|---|---|---|
| WO | WO9802740 * | 1/1998 |
| WO | 98/59042 A1 | 12/1998 |
| WO | 00/06780 A1 | 2/2000 |
| WO | 00/75647 | 12/2000 |
| WO | 00/77235 | 12/2000 |
| WO | 01/79851 | 10/2001 |
| WO | 01/98542 | 12/2001 |
| WO | 02/055985 | 7/2002 |
| WO | 03/018757 A2 | 3/2003 |
| WO | 03/019141 A2 | 6/2003 |
| WO | 03/069344 | 8/2003 |
| WO | 03/095974 | 11/2003 |
| WO | 2006/083286 A2 | 8/2006 |
| WO | WO2006083286 * | 8/2006 |
| WO | 2006/100063 A2 | 9/2006 |
| WO | 2007/022483 A2 | 2/2007 |
| WO | 2008/107724 A2 | 9/2008 |
| WO | 2008/157203 A2 | 12/2008 |
| WO | WO2008157203 * | 12/2008 |
| WO | 2010/096323 A1 | 8/2010 |
| WO | 2010/123908 A1 | 10/2010 |
| WO | 2011/014741 A1 | 2/2011 |
| WO | 2011/057184 | 5/2011 |
| WO | 2011/082415 A2 | 7/2011 |
| WO | 2013/086428 A1 | 6/2013 |
| WO | 2013/123030 A2 | 8/2013 |

OTHER PUBLICATIONS

Du N et al: "Generation and evaluation of the trivalent inactivated reassortant vaccine using human, avian, and swine influenza A viruses", Vaccine, Elsevier LTD, GB, vol. No. 2 Jun. 2008 pp. 2912-2918, XP022566986, ISSN:0254-410X, DOI: 10.1016/J.Vaccine.2008.03.048[retrieved on Apr. 11, 2008] abstract p. 2914, left-hand column, paragraph 2.

Vincent A L et al: "Efficacy of inactivated swine influenza virus vaccines against the 2009 A/H1H1 Influenza Virus in Pigs", Vaccine, vol. 28, No. 15, Mar. 24, 2010, pp. 2782-2787, XP026946263,ISSN: 0264-410X, DOI: 10.1016/J.Vaccine. 2010. 01.049 [Retrieved on Feb. 2, 2010]abstract.

International Preliminary Report on Patentability dated Aug. 16, 2013 (PCT/US2012/036304).

Allan et al., A Standard Haemaggiutination Inhibition Test for Newcastle Disease, (2) Vaccination and Challenge. Vet Rec., Aug. 17, 1974, 147-149, 95, 7.

Almond, J., Vaccine Renaissance, Nature Reviews Microbiology, Jul. 2007, 478-481, 5.

Bahnemann, H.G., Binary Ethylenimine as an Inactivant for Foot-and-Mouth Disease Virus and Its Application for Vaccine Production, Archives of Virology, 1975, 47-56.

(56) References Cited

OTHER PUBLICATIONS

Barteling, S. et al., Formaldehyde enhances BEI-inactivation rates of Foot-and-Mouth Disease (FMD) virus by at least a ten fold, Report ; European Commission for the Control of Foot-and-Mouth Disease. Research Group of the Standing Technical Committee, Sep. 2000, 270-275, Appendix 34, Bulgaria.
Cussac, C. et al., Reduction of the toxicity and mutagenicity of aziridine in mammalian cells harboring the *Escherichia Coli* fpg gene, Nucleic Acids Research, 1996, 1742-1746, 24, 9.
De Swart, R. et al., Immunization of Macaques with Formalin-Inactivated Respiratory Syncytial Virus (RSV) Induces Interleukin-13-Associated Hypersensitivity to Subsequent RSV Infection, Journal of Virology, Nov. 2002, 11561-11569, 76, 22.
Durham, An END for Exotic Newcastle Disease Virus?, Agricultural Research, Oct. 2008, 20-21, 51, 10.
Exotic Newcastle Disease Fact Sheet, National Agricultural Biosecurity Center, Available at: http://nabc.ksu.edu/content/factsheets/category/Exotic%20Newcastle%20Disease last accessed Aug. 17, 2011.
Grimes, S., Titrating Newcastle disease virus for infectivity. A Basic Laboratory Manual for The Small-Scale Production and Testing of I-2 Newcastle Disease Vaccine, 2002, 73-79.
Habib, M. et al., Inactivation of infectious bursal disease virus by binary ethylenimine and fomaline, Journal of Zhejiang University Science B, 2006, 320-323, 7, 4.
Kapczynski, D. R. et al., Protection of Chickens Against Overt Clinical Disease and Determination of Viral Shedding Following Vaccination with Commercially Available Newcastle Disease Virus Vaccines upon Challenge with Highly Virulent Virus from the California 2002 Exotic Newcastle Disease Outbreak, Vaccine, May 2005, 3424-3433, 23, 26.
Larghi, O. et al., Rabies Virus Inactivation by Binary Ethylenimine: New Method for Inactivated Vaccine Production, Journal of Clinical Microbiology, Feb. 1980, 120-122, 11, 2.
Moghaddam, A. et al., A potential molecular mechanism for hyperactivity caused by formalin-inactivated vaccines, Nature Medicine, Aug. 2006, 905-907, 12, 8.
Offit, P. et al., Addressing Parents' Concerns: Do Vaccines Contain Harmful Preservatives, Adjuvants, Additives, or Residuals?, Pediatrics, Dec. 2003, 1394-1401, 112, 6.
Peebles, R. et al., Respiratory Syncytial Virus (RSV)—Induced Airway Hyperresponsiveness in Allergically Sensitized Mice Is Inhibited by Live RSV and Exacerbated by Formalin-Inactivated RSV, Journal of Infectious Diseases, 2000, 671-677, 182.
Sheridan, C., Production technologies change flu vaccine landscape, Nature Biotechnology, Jul. 2, 2007, 701, 25.
Sun, I. et al., Comparison of Pseudorabies Virus Inactivated by Bromo-Ethylene-Imine, Co Irradiation and Acridine Dye in Immune Assay Systems, Journal of Clinical Microbiology, Nov. 1978, 604-611, 8, 5.
Takimoto, T. et al., Role of the Hemagglutinin-Neuraminidase Protein in the Mechanism of Paramyxovirus-Cell Membrane Fusion, J Virology, Dec. 2002, 13028-13033, 76, 24.
Van Boven, M et al., Herd Immunity to Newcastle Disease Virus in Poultry by Vaccination, Avian Pathology, Feb. 2008, 1-5, 37, 1.
International Search Report & Written Opinion for Application No. PCT/US2014/047551, dated Oct. 23, 2014.
Written Opinion from the European Patent Office for Application No. PCT/US2014/047551, dated Sep. 14, 2015.
International Preliminary Report on Patentability for Application No. PCT/US2014/047551, dated Dec. 10, 2015.
Rait, "Conversions of formaldehyde-modified 2'-deoxyadenosine 5'-monophosphate in conditions modeling formalin-fixed tissue dehydration" J. Histochem Cytochem 54(3): 301-10, (Mar. 1, 2006).
Lee, Thomas "Down Syndrome and Cell-Free Fetal DNA in Archived Maternal Serum" (AM J. Obstet Gynecol 2002; 187: 1217-21).
Lo et al."Fetal Cell-Free Plasma DNA Concentrations in Maternal Blood are Stable 24 hours after" Clinical-Chemistry (Jan. 19, 2012).
Lo, Y M Dennis, "Fetal Nucleic Acids in Maternal Plasma, Toward the Development of Noninvasive Prenatal Diagnosis of Fetal Chromosomal Aneuploidies," 2008 New York Academy of Sciences.
Wagner, J, "Free DNA—new potential analyte in clinical laboratory diagnostics?" Biochem Med (Zagreb) 22(1): 24-38, 2006.
Dhallan et al., "Methods to Increase the Percentage of Free Fetal DNA Recovered from the Maternal Circulation," JAMA 291, 1114-1119, Mar. 3, 2004.
Chinnapapagari et al., "Treatment of Material Blood Samples with Formaldehyde does not alter the Proportion of Circulatory Fetal Nucleic Acids (DNA and mRNA) in Maternal Plasma", Technical Briefs, University Women's Hospital/Dept. of Research, Basel, Switzerland, pp. 652-655, 2005.
A Sample Preparation and Analysis System for Indentification of Circulating Tumor Cells; vol. 25, No. 1; Spring 2002; Journal of Clinical Ligand Assay.
Bianchi et al., "PCR Quantification of Fetal Cells in Maternal Blood in Normal and Aneuploid Pregnancies" Am J. Hum. Genet. 61:822-829, 1997.
American Association for Cancer Research; 93ra Annual Meeting; Apr. 6-10, 2002; San Francisco, California; vol. 43, Mar. 2002.
Annals of the New York Academy of Sciences: Circulating Nucleic Acids in Plasma or Serum II, vol. 945, Issue pp. 1-291 (Sep. 2001).
Ashoor, G et al., "Trisomy 13 detection in the first trimester of pregnancy using a chromosome-selective cell-free DNA analysis method" Ultrasound in Obstetrics & Gynecology; 41(1):21-5, Nov. 23, 2012.
Barrett et al., "Implementing Prenatal Diagnosis Based on Cell-Free Fetal DNA: Accurate Identification of Factors Affecting Fetal DNA Yield," PLoS One, 6(10):e25202, Oct. 4, 2011.
Bayindir, B et al., "Noninvasive Prenatal Testing Using a Novel Analysis Pipeline to Screen for All Autosomal Fetal Aneuploidies Improves Pregnancy Management," European Journal of Human Genetics. Jan. 14, 2015.
Beck, J et al., Digital Droplet PCR for Rapid Quantification of Donor DNA in the Circulation of Transplant Recipients as a Potential Universal Biomarker of Graft Injury. Clinical chemistry; 59(12):1732-41, Dec. 1, 2013.
Benachi, A et al., Cell-Free DNA Analysis in Maternal Plasma in Cases of Fetal Abnormalities Detected on Ultrasound Examination. Obstetrics & Gynecology; 125(6):1330-7, Jun. 1, 2015.
Bethel, K et al., "Fluid phase biopsy for detection and characterization of circulating endothelial cells in myocardial infarction," Physical biology; 11(1):016002, Feb. 1, 2014.
Bevilacqua, E et al., "Performance of screening for aneuploidies by cell-free DNA analysis of maternal blood in twin pregnancies," Ultrasound in Obstetrics & Gynecology; 45(1):61-6, Jan. 1, 2015.
Bianchi, DW et al., "DNA sequencing versus standard prenatal aneuploidy screening" New England Journal of Medicine;370(9):799-808, Feb. 27, 2014.
Bianchi, D et al., "Fetal sex chromosome testing by maternal plasma DNA sequencing: clinical laboratory experience and biology," Obstetrics & Gynecology; 125(2):375-82, Feb. 1, 2015.
Bianchi, "Invited Editorial Fetal DNA in Maternal Plasma: The Plot Thickens and the Placental Barrier Thins," The American Society of Human Genetics, 62:763-764, 1998.
Bina-Stein, et al., Aurintricarboxylic Acid Is a Nonspecific Enzyme Inhibitor, Department of Chemistry, Yale University, New Haven, Connecticut. 1975, 12:191-193.
Biocept—Expands Patent Protection for Liquid Biopsy Platform dated Jun. 1, 2015; http://ir.biocept.com/releasedetail.cfm?releaseID=915635.
Biocept (BIOC) Announces Patent for Blood Collection and Transport Tube; StreetInsider.com; http://www.streetinsider.com/corporate+news/biocept+(BIOC)+Announces; Jun. 1, 2015.
Bioreceptor Fenofiuids: Novel Characteristics and their Utility in Medical Applications; P. A. Liberti, J. N. Chiarappa, A. C. Hovespian, C. G. Rao; Supplied by the British Library; 1996 Kluwer Academic Publishers.
Brar, H et al., "The fetal fraction of cell-free DNA in maternal plasma is not affected by a priori risk of fetal trisomy," The Journal of Maternal-Fetal & Neonatal Medicine; 26(2):143-5, Jan. 1, 2013.

(56) References Cited

OTHER PUBLICATIONS

Bruno, D et al., Use of copy number deletion polymorphisms to assess DNA chimerism. Clinical chemistry; 60(8):1105-14, Aug. 1, 2014.

Buysse, K et al. "Reliable noninvasive prenatal testing by massively parallel sequencing of circulating cell-free DNA from maternal plasma processed up to 24h after venipuncture," Clinical biochemistry; 46(18):1783-6, Dec. 31, 2013.

Carlsson, A et al., "Circulating Tumor Microemboli Diagnostics for Patients with Non—Small-Cell Lung Cancer," Journal of Thoracic Oncology; 9(8):1111-97, Aug. 1, 2014.

Chan et al, "Hypermethylated RASSFIA in maternal Plasma: A Universal Fetal DNA Marker that Improves the Reliability of Noninvasive Prenatal Diagnosis," Clinical Chemistry, 2211-2218, 52(12), 2006.

Chudziak, J et al., "Clinical evaluation of a novel microfluidic device for epitope-independent enrichment of circulating tumour cells in patients with small cell lung cancer," The Analyst;141(2):669-78, Nov. 2015.

Lo, Y M Dennis"Circulating Nucleic Acids in Plasma and Serum: An Overview", (2001).

Clark-Ganheart et al., "Use of Cell-Free DNA in the Investigation of Intrauterine Fetal Demise and Miscarriage," Obstetrics & Gynecology; 125(6):1321-9, Jun. 1, 2015.

Zhang, Yi et al., "Effect of Formaldehyde Treatment on the recovery of cell-free fetal DNA from Maternal Plasma at Different Processing Times" Clinic Chimica Acta 397, 60-64, 2008.

Clinical Applications of Flow Cytometry: Immunophenotyping of Leukemic Cells; Approved Guideline; Jun. 1998; vol. 18 No. 8; NCCLS.

Lo, et al., "Increased Fetal DNA Concentrations in the Plasma of Pregnant Women Carrying Fetuses with Trisomy 21" Clinical Chemistry 45:10, 1747-1751 (1999).

Lo, Y M Dennis "Molecular Testing of Urine: Catching DNA on the way out" Clinical Chemistry 46, No. 8, 2000.

Botezatu et al. "Genetic Analysis of DNA Excreted in Urine: A New Approach for Detecting Specific Genomic DNA Sequences from Cells Dying in an Organism" Clinical Chemistry 46:8, 1078-1084 (2000).

Chiu, Rosa et al.,"Effects of Blood-Processing Protocols on Fetal and Total DNA Quantification in Maternal Plasma," Clinical Chemistry 47:9, 1607-1613, 2001.

Chung et al., "Lack of Dramatic Enrichment of Fetal DNA in Maternal Plasma by Formaldehyde Treatment," Clinical Chemistry, 51, No. 3, 2005.

Comas, C et al., "Initial Experience with Non-Invasive Prenatal Testing of Cell-Free DNA for Major Chromosomal Anomalies in a Clinical Setting," The Journal of Maternal-Fetal & Neonatal Medicine; (0):1-6, Aug. 12, 2014.

Curnow et al., "Detection of Triploid, Molar, and Vanishing Twin Pregnancies by a Single-Nucleotide Polymorphism—Based Noninvasive Prenatal Test," American Journal of Obstetrics and Gynecology, 212(1):79-e1 Jan. 2015.

Dash et al. "Using Noninvasive Prenatal Testing for Aneuploidies in a Developing Country: Lessons Learnt" Journal of Fetal Medicine, 1(3):131-5, 2014.

Denis et al. "Efficient Detection of BRAF Mutation in Plasma of Patients after Long-term Storage of Blood in Cell-Free DNA Blood Collection Tubes" Clinical Chemistry, 61(6):886-8, Jun. 1, 2015.

Chung et al.; "Detrimental Effect of Formaldehyde on Plasma RNA Detection" 51 (6): 10, Jul. 12, 2010.

Dharajiya et al. "Noninvasive Prenatal Testing Using Cell-Free Fetal DNA in Maternal Plasma" Current Protocols in Human Genetics, 8-15, Jan. 20, 2015.

Diamond et al. "Diverse and Targetable Kinase Alterations Drive Histiocytic Neoplasms" Cancer discovery: CD-15, Nov. 15, 2015.

Ding, et al., MS Analysis of Single-Nucleotide Differences in Circulating Nucleic Acids: Application to Noninvasive Prenatal Diagnosis, 101:10762-10767, 2004.

Fairbrother et al. "Clinical experience of noninvasive prenatal testing with cell-free DNA for fetal trisomies 21, 18, and 13, in a general screening population" Prenatal Diagnosis; 33(6):580-3, Jun. 1, 2013.

Futch et al. "Initial clinical laboratory experience in noninvasive prenatal testing for fetal aneuploidy from maternal plasma DNA samples" Prenatal Diagnosis; 33(6):569-74, Jun. 1, 2013.

Gil et al. "Cell-free DNA analysis for trisomy risk assessment in first-trimester twin pregnancies" Fetal Diagnosis and Therapy; 35(3):204-11, Nov. 15, 2013.

Gil et al. "LK NHS pilot study on cell-free DNA testing in screening for fetal trisomies: factors affecting uptake" Ultrasound in Obstetrics & Gynecology; 45(1):67-73. Jan. 1, 2015.

Gil et al. "Implementation of maternal blood cell-free DNA testing in early screening for aneuploidies" Ultrasound in Obstetrics & Gynecology; 42(1):34-40, Jun. 7, 2013.

Gonzalez, et al., "Application of Fetal DNA Detection in Maternal Plasma: A Prenatal Diagnosis Unit Experience," Journal of Histochemistry & Cytochemistry, 53(3): 307-314, 2005.

Grömminger et al. "Fetal aneuploidy detection by cell-free DNA sequencing for multiple pregnancies and quality issues with vanishing twins" Journal of Clinical Medicine; 3(3):679-92, Jun. 25, 2014.

Gross et al. "Rapid changes in circulating tumor cells following anti-angiogenic therapy" Convergent Science Physical Oncology; 1(1):015002, Sep. 15, 2015.

Hidestrand et al. "Influence of temperature during transportation on cell-free DNA analysis" Fetal diagnosis and Therapy; 31(2):122-8, 2012.

Hindson et al. "High-throughput droplet digital PCR system for absolute quantitation of DNA copy number" Analytical Chemistry; 83(22):8604-10, Oct. 28, 2011.

Holford et al, "Stability of beta-actin mRNA in plasma," Annals of the New York Academy of Science, 108-111, 1137, Aug. 2008.

Holmberg et al. "Akonni TruTip® and Qiagen® methods for extraction of fetal circulating DNA—evaluation by real-time and digital PCR" PloS One; 8(8):e73068, Aug. 2013.

Hooks et al. "Non-invasive risk assessment of fetal sex chromosome aneuploidy through directed analysis and incorporation of fetal fraction" Prenatal Diagnosis; 34(5):496-9, May 2014.

http://ir.biocept.com/secfiling.cfm?filingid=1193125-15-16425 &cik=1044378; Biocept Completing the Answer; Jan. 21, 2015.

Hynek et al., "MoM-based Approach to Noninvasive Prenatal Testing Using Exponentially Weighted Moving Average Chart and Chromosomal Fingerprint" International Journal of Biomedicine and Healthcare: 12, 2015.

Ignatiadis et al. "Circulating Tumor Cells and Circulating Tumor DNA: Challenges and Opportunities on the Path to Clinical Utility" Clinical Cancer Research; 21 (21): 4786-800, Nov. 2015.

Jensen et al. "High-throughput massively parallel sequencing for fetal aneuploidy detection from maternal plasma" PloS One; 8(3): e57381, Mar. 2013.

Jeon et al. "The feasibility study of non-invasive fetal trisomy 18 and 21 detection with semiconductor sequencing platform" PLoS One; 9(10):e110240, Oct. 20, 2014.

Juneau et al. "Microarray-based cell-free DNA analysis improves noninvasive prenatal testing" Fetal Diagnosis and Therapy; 36(4):282-6, 2014.

Kadam et al. "Quantitative measurement of cell-free plasma DNA and applications for detecting tumor genetic variation and promoter methylation in a clinical setting" The Journal of Molecular Diagnostics. Jul. 31, 2012;14(4):346-56.

Katz et al. No Date. "Mass-Volume Equivalents of Common Chemical Solids." Available at <http://www.chymist.com/Mass-volume %20equivalents.pdf>. Accessed Oct. 22, 2015. 4 pages.

Kidess et al. "Mutation profiling of tumor DNA from plasma and tumor tissue of colorectal cancer patients with a novel, high-sensitivity multiplexed mutation detection platform" Oncotarget. Feb. 2015; 6(4):2549.

Kirkizlar et al. "Detection of Clonal and Subclonal Copy-Number Variants in Cell-Free DNA from Patients with Breast Cancer Using a Massively Multiplexed PCR Methodology" Translational oncology. Oct. 31, 2015;8(5):407-16.

(56) References Cited

OTHER PUBLICATIONS

Kwee et al. "Measurement of Circulating Cell-Free DNA in Relation to 18F-Fluorocholine PET/CT Imaging in Chemotherapy-Treated Advanced Prostate Cancer" Clinical and Translational Science. Feb. 1, 2012;5(1):65-70.

Lambert-Messerlian et al. "Feasibility of using plasma rather than serum in first and second trimester multiple marker Down's syndrome screening. Journal of medical screening" Dec. 1, 2012;19(4):164-70.

Lanman et al.. "Analytical and clinical validation of a digital sequencing panel for quantitative, highly accurate evaluation of cell-free circulating tumor DNA" PloS one. Oct. 16, 2015;10(10):e0140712.

Lee et al., "Survival of Donor Leukocyte Subpopulations in Immunocompetent Transfusion Recipients: Frequent Long-Term Microchimerism in Severe Trauma Patients," Blood, 3127-3139, 93, 1999.

Lee et al. "Performance of Momguard, a new non-invasive prenatal testing protocol developed in Korea" Obstetrics & Gynecology Science. Sep. 1, 2015;58(5):340-5.

Li, et al., "Detection of Paternally Inherited Fetal Point Mutations for β-Thalassemia Using Size-Fractionated Cell-Free DNA in Maternal Plasma," available at: www.jama.com, 293:843-849, 2005.

Liao et al. "Noninvasive prenatal diagnosis of common aneuploidies by semiconductor sequencing" Proceedings of the National Academy of Sciences. May 20, 2014;111(20):7415-20.

Liu et al. "Placental mosaicism for Trisomy 13: a challenge in providing the cell-free fetal DNA testing" Journal of assisted reproduction and genetics. May 1, 2014;31(5):589-94.

Lo et al., "Noninvasive prenatal diagnosis for fetal chromosomal aneuploidies by maternal plasma nucleic acid analysis" Clinical Chemistry, American Association for Clinical Chemistry, Washington DC Lnkd-Doi:10.1373/Clinchem.2007.100016, vol. 54, No. 3, pp. 461-466, Jan. 17, 2008.

Lo, et al., "Quantitative Analysis of Fetal DNA in Maternal Plasma and Serum: Implications for Noninvasive Prenatal Diagnosis," by The American Society of Human Genetics, 62:768-775, 1998.

Lo, "Fetal DNA in Maternal Plasma: Biology and Diagnostic Applications," Clinical Chemistry 46:12 1903-1906, 2000.

Lu et al. Detection and Characterization of Circulating Tumour Cells from Frozen Peripheral Blood Mononuclear Cells. Journal of Circulating Biomarkers. Dec. 1, 2015;35(12):1243-6.

Machaca et al., "Characterization of apoptosis-like endonuclease activity in avian thymocytes," Biology of the Cell, 15-22, 76(1), Elsevier, Paris France, Jan. 1, 1992.

Madabusi et al., "RNA extraction for Arrays," Methods in Enzymology, 1-14, 411, 2006.

Mccullough et al. "Non-invasive prenatal chromosomal aneuploidy testing-clinical experience: 100,000 clinical samples" PLoS One. Oct. 7, 2014;9(10):e109173.

Nair et al. "An observational study of circulating tumor cells and (18) F-FDG PET uptake in patients with treatment-naive non-small cell lung cancer" PloS One. Jul. 5, 2013;8(7):e67733.

Nicolaides et al. "Validation of targeted sequencing of single-nucleotide polymorphisms for non-invasive prenatal detection of aneuploidy of chromosomes 13, 18, 21, X, and Y" Prenatal Diagnosis. Jun. 1, 2013;33(6):575-9.

Norton et al. "Non-Invasive Chromosomal Evaluation (NICE) Study: results of a multicenter prospective cohort study for detection of fetal trisomy 21 and trisomy 18" American Journal of Obstetrics and Gynecology. Aug. 31, 2012;207(2):137-e1.

Norton et al. "Cell-free DNA analysis for noninvasive examination of trisomy" New England Journal of Medicine. Apr. 23, 2015;372(17):1589-97.

Ono et al. "Circulating microRNA Biomarkers as Liquid Biopsy for Cancer Patients: Pros and Cons of Current Assays" Journal of clinical medicine. Oct. 23, 2015;4(10):1890-907.

Palmer et al., "Flow cytometric determination of residual white blood cell levels in preserved samples from leukoreduced blood products," Transfusion, 118-128, 48(1), Jan. 2008.

Pan, et al., "Cell-free Fetal DNA Levels in Pregnancies Conceived by IVF", Human Reproduction, 20(11):3152-3156, 2005.

Persico et al. "Cell-free DNA testing in the maternal blood in high-risk pregnancies after first trimester combined screening" Prenatal Diagnosis. Jan. 1, 2016.

Pertl, et al., "Fetal DNA in Maternal Plasma: Emerging Clinical Applications," by The American College of Obstetricians and Gynecologists, 98:483-490, 2001.

Pinzani et al., "Circulating Nucleic Acids in Cancer and Pregnancy," Methods: A Companion to Methods in Enzymology, 302-307, 40 (4), Academic Press Inc., New York, Apr. 1, 2010.

Sekizawa et al.; "Apoptosis in Fetal Nucleated Erythrocytes Circulating in Maternal Blood" Prenatal Diagnosis; 20: 886-889, 2000.

Punnoose et al. "PTEN loss in circulating tumour cells correlates with PTEN loss in fresh tumour tissue from castration-resistant prostate cancer patients" British Journal of Cancer. Oct. 20, 2015;113(8):1225-33.

Puren et al., Laboratory operations, specimen processing, and handling for viral load testing and surveillance, Journal of Infectious Diseases, S27-S36, 201(supp 1), University of Chicago Press, Chicago II, Apr. 15, 2010.

Quezada et al. "Fetal fraction of cell-free DNA in maternal plasma in the prediction of spontaneous preterm delivery." Ultrasound in Obstetrics & Gynecology. Jan. 1, 2015;45(1):101-5.

Quezada et al. "Screening for trisomies 21, 18 and 13 by cell-free DNA analysis of maternal blood at 10-11 weeks' gestation and the combined test at 11-13 weeks" Ultrasound in Obstetrics & Gynecology. Jan. 1, 2015;45(1):36-41.

Risberg B. "Establishment of PCR based methods for detection of ctDNA in blood." Thesis submitted for the Master's degree in Biomedicine. Oslo University Hospital, Institute for Cancer Research, Department of Genetics and Oslo and Akershus University College of Applied Sciences. May 5, 2013.

Ruiz et al. "Limited genomic heterogeneity of circulating melanoma cells in advanced stage patients" Physical Biology. Feb. 1, 2015;12(1):016008.

Salvianti et al. "Single circulating tumor cell sequencing as an advanced tool in cancer management" Expert review of molecular diagnostics. Nov. 27, 2015:1-3.

Samango-Sprouse et al. "SNP-based non-invasive prenatal testing detects sex chromosome aneuploidies with high accuracy" Prenatal diagnosis. Jul. 1, 2013;33(7):643-9.

Samoila et al. "Method development and validation for clinical cfDNA extraction from blood" InASCO Annual Meeting Proceedings May 20, 2015 (vol. 33, No. 15_suppl, p. e22185).

Samuel et al. "The effect of chorionic villus sampling on the fraction of cell-free fetal DNA in maternal plasma" The Journal of Maternal-Fetal & Neonatal Medicine. Oct. 15, 2015:1-4.

Scheffer et al. "Noninvasive fetal blood group genotyping of rhesus D, c, E and of K in alloimmunised pregnant women: evaluation of a 7-year clinical experience" BJOG: An International Journal of Obstetrics & Gynaecology. Oct. 1, 2011;118(11):1340-8.

Schiavon et al. "Analysis of ESR1 mutation in circulating tumor DNA demonstrates evolution during therapy for metastatic breast cancer" Science translational medicine. Nov. 11, 2015;7(313):313ra182-.

Seo et al. "An Experience of Using the Harmony Test for Genomics-Based Non-Invasive Prenatal Testing" Journal of Laboratory Medicine and Quality Assurance. Mar. 1, 2015;37(1):44-6.

Shi et al. "Feasibility of noninvasive prenatal testing for common fetal aneuploidies in an early gestational window" Clinica Chimica Acta. Jan. 15, 2015;439:24-8.

Sigma-Aldrich. "1-Aza-3,7-dioxabicyclo[3.3.0]octane-5-methanol solution." Available online at www.sigmaaldrich.com/catalog/product/aldrich/417807?lang=en&region=US. 5 pages. Accessed Jan. 13, 2014.

Sillence, et al. "Fetal Sex and RHD Genotyping with Digital PCR Demonstrates Greater Sensitivity than Real-time PCR" Clinical Chemistry. Nov. 1, 2015;61(11):1399-407.

(56) References Cited

OTHER PUBLICATIONS

Smid et al., "Quantitative Analysis of Fetal DNA in Maternal Plasma in Pathological Conditions Associated with Placental Abnormalities," Annals New York Academy of Sciences, 951:133-137, 2001.
Song et al. "Non-invasive prenatal testing for fetal aneuploidies in the first trimester of pregnancy" Ultrasound in Obstetrics & Gynecology. Jan. 1, 2015;45(1):55-60.
Sparks et al. "Noninvasive prenatal detection and selective analysis of cell-free DNA obtained from maternal blood: evaluation for trisomy 21 and trisomy 18" American Journal of Obstetrics and Gynecology. Apr. 30, 2012;206(4):319-e1.
Sparks et al. "Selective analysis of cell-free DNA in maternal blood for evaluation of fetal trisomy" Prenatal Diagnosis. Jan. 1, 2012;32(1):3-9.
Stokowski et al. "Clinical performance of non-invasive prenatal testing (NIPT) using targeted cell-free DNA analysis in maternal plasma with microarrays or next generation sequencing (NGS) is consistent across multiple controlled clinical studies" Prenatal Diagnosis. Dec. 1, 2015;35(12):1243-6.
Stumm et al. "Diagnostic accuracy of random massively parallel sequencing for non-invasive prenatal detection of common autosomal aneuploidies: a collaborative study in Europe" Prenatal Diagnosis. Feb. 1, 2014;34(2):185-91.
Takabayashi et al. "Development of Non-invasive Fetal DNA Diagnosis from Maternal Blood," Prenatal Diagnosis, 15:74-77, 1995.
Smid et al., "Evaluation of Different Approaches for Fetal DNA Analysis from Maternal Plasma and Nucleated Blood Cells", Technical Briefs, pp. 1570-1572, 1999.
Thung et al. "Implementation of whole genome massively parallel sequencing for noninvasive prenatal testing in laboratories" Expert Review of Molecular Diagnostics. Jan. 2, 2015;15(1):111-24.
Toro. "Detection of PIK3CA Mutations in Plasma Tumor DNA Circulating in Peripheral Blood of Breast Cancer Patients" Thesis submitted for the degree of Master of Science in Molecular and Cellular Biology. Johns Hopkins University, Baltimore, Maryland. Apr. 2014.
Toro et al. "Comparison of cell stabilizing blood collection tubes for circulating plasma tumor DNA" Clinical Biochemistry. Oct. 31, 2015;48(15):993-8.
Tynan et al. Application of risk score analysis to low-coverage whole genome sequencing data for the noninvasive detection of trisomy 21, trisomy 18, and trisomy 13. Prenatal diagnosis. Jan. 1, 2015.
US Food and Drug Adminstration, "Draft Guidance for Industry: Pre-Storage Leukocyte Reduction of Whole Blood and Blood Components Intended for Transfusion, Vaccines." Blood & Biologics, available at: www.fda.gov/biologicsbloodvaccines/guidance complianceregulatoryinformation/guidances/blood/ucm076769. htm, last accessed Apr. 13, 2011.
Vandenberghe et al. "Non-invasive detection of genomic imbalances in Hodgkin/Reed-Sternberg cells in early and advanced stage Hodgkin's lymphoma by sequencing of circulating cell-free DNA: a technical proof-of-principle study" The Lancet Haematology. Feb. 28, 2015;2(2):e55-65.
Verweij et al. "European Non-Invasive Trisomy Evaluation (EU-NITE) study: a multicenter prospective cohort study for non-invasive fetal trisomy 21 testing" Prenatal Diagnosis. Oct. 1, 2013;33(10):996-1001.
Wang D et al. Exploring Glycan Markers for Immunotyping and Precision—targeting of Breast Circulating Tumor Cells. Archives of medical research. Dec. 1, 2015.
Wang E et al. "Gestational age and maternal weight effects on fetal cell-free DNA in maternal plasma" Prenatal diagnosis. Jul. 1, 2013;33(7):662-6.
Wang P et al. "Sensitive detection of mono-and polyclonal ESR1 mutations in primary tumors, metastatic lesions and cell free DNA of breast cancer patients" Clinical Cancer Research. Oct. 23, 2015:clincanres-1534.
Wang Q et al. "Real-time PCR evaluation of cell-free DNA subjected to various storage and shipping conditions" Genetics and Molecular Research. Jan. 1, 2015;14(4):12797-804.
Wang Y et al. "Maternal mosaicism is a significant contributor to discordant sex chromosomal aneuploidies associated with noninvasive prenatal testing" Clinical chemistry. Jan. 1, 2014;60(1):251-9.
Werner et al. "Analytical Validation and Capabilities of the Epic CTC Platform: Enrichment-Free Circulating Tumour Cell Detection and Characterization" Journal of Circulating Biomarkers. 2015 4:3.
Wienzek-Lischka et al. "Noninvasive fetal genotyping of human platelet antigen-la using targeted massively parallel sequencing" Transfusion Apr. 1, 2015.
Willems et al. "The first 3,000 non-invasive prenatal tests (NIPT) with the harmony test in Belgium and the Netherlands" Facts, Views & Vision in ObGyn. 2014;6(1):7.
Wong et al. "Optimizing blood collection, transport and storage conditions for cell free DNA increases access to prenatal testing" Clinical Biochemistry. Aug. 31, 2013;46(12):1099-104.
Woolcock et al. "Noninvasive prenatal testing." Australian Family Physician. Jul. 1, 2014;43(7):432.
Lo et al. "Presence of Fetal DNA in Maternal Plasma and Serum" The Lancet, 350, 485-87, 1997.
Zill, et al. "Cell-free DNA next-generation sequencing in pancreatobiliary carcinomas" Cancer discovery. Oct. 1, 2015;5(10):1040-8.
European Communication dated May 25, 2016; Application No. 13706856.5.
European Office Action, Application No. 13706856.5 dated Mar. 10, 2016.
European Office Action for Application No. 13706856.5 dated May 27, 2015.
European Patent Office Summons to Attend dated Jan. 27, 2016 for Application No. 10704474.5.
European Office Action dated Nov. 17, 2014 for Application No. 10704474.5.
European Communication dated Aug. 30, 2016 for Application No. 10704474.5.
Wiebe et al., "Inhibition of Cell Proliferation by Glycerol" Life Sci., 1991, 48(16): 1511-7.
Canadian Office Action dated Oct. 13, 2016; Application No. 2,780,536.
Extended European Search Report dated Oct. 21, 2016; Application No. 15196213.1.
Hossain, Mozaffor K.M., Anitbody Levels Against Newcastle Disease Virus In Chickens In Rajshahi and Surrounding Districts of Bangladesh; www.ccsenet.org/ijb; International Journal of Biology, vol. 2, dated Jul. 2010.
US Office Action, U.S. Appl. No. 12/940,112 dated Aug. 15, 2016.
US Office Action, U.S. Appl. No. 12/940,112 dated Nov. 13, 2012.
US Office Action, U.S. Appl. No. 12/940,112 dated May 28, 2013.
Cold Spring Harbor Protocols, Recipe for Phosphate-buffered saline (PBS), 2006, 1 page printout on Aug. 12, 2016, available from http://cshprotocols.cshlp.org/content/2006/1/pdb.rec8247.
US Appeal Decision, U.S. Appl. No. 12/940,112 dated May 31, 2016.

\* cited by examiner

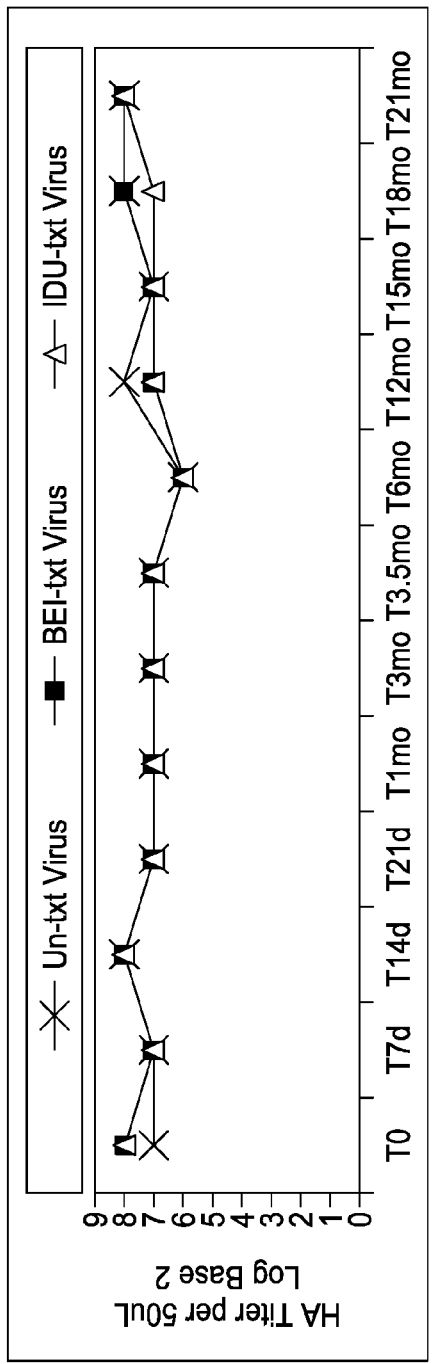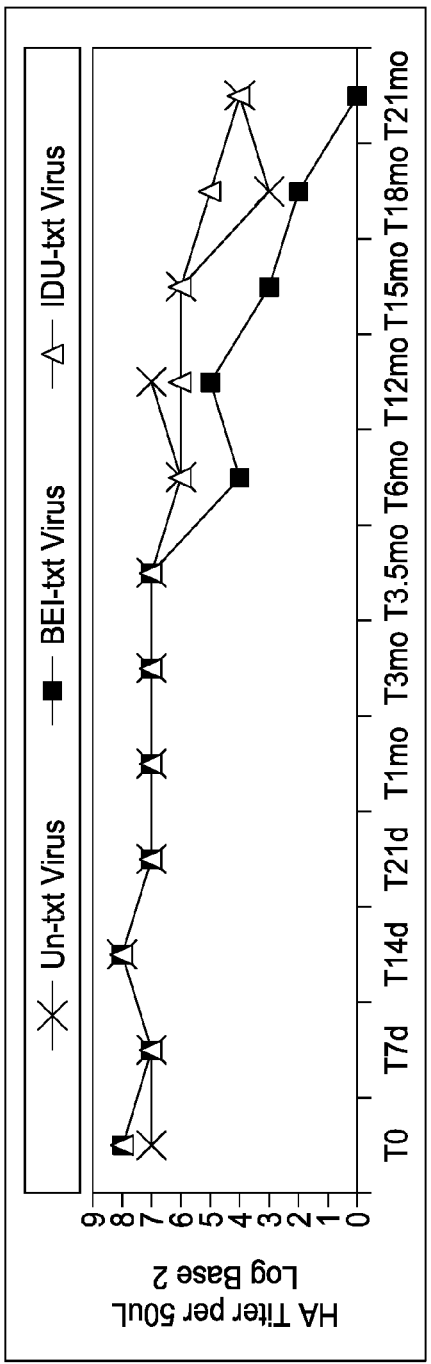

Fig-3: Hemagglutination Bio-Activity of H1N2 SIV Isolate Stored at 2-7 °C

Fig-4: Hemagglutination Bio-Activity of H1N2 SIV Isolate Stored at 22-25 °C

Fig-5

Hemagglutination Bio-Activity of H1N2 SIV Isolate Stored at 35-39°C

Fig-6

Hemagglutination Bio-Activity of H1N2 SIV Isolate Stored at 40-42°C

Fig-7

Hemagglutination Bio-Activity of H3N2 SIV Isolate Stored at 2-7 °C

Fig-8

Hemagglutination Bio-Activity of H3N2 SIV Isolate Stored at 22-25 °C

Fig-9. Hemagglutination Bio-Activity of H3N2 SIV Isolate Stored at 35-39°C

Fig-10. Hemagglutination Bio-Activity of H3N2 SIV Isolate Stored at 40-42°C

Fig-11: Hemagglutination Bio-Activity of H3N2 SIV Isolate Inactivated with 0.5% IDU and Stored at 2-7°C Fig-12: Hemagglutination Bio-Activity of H3N2 SIV Isolate Inactivated with 0.5% IDU and Stored at 35-39°C

Fig-15

Hemagglutination Bio-Activity of H1N2 SIV Isolate Inactivated with 0.5% IDU and Stored at 35-39°C

Fig-16

Hemagglutination Bio-Activity of H1N2 SIV Isolate Inactivated with 0.5% IDU and Stored at 40-42°C

Fig-17

Hemagglutination Bio-Activity of H1N2 SIV Isolate Inactivated with 1.0% IDU and Stored at 2-7°C

Fig-18

Hemagglutination Bio-Activity of H1N2 SIV Isolate Inactivated with 1.0% IDU and Stored at 35-39°C

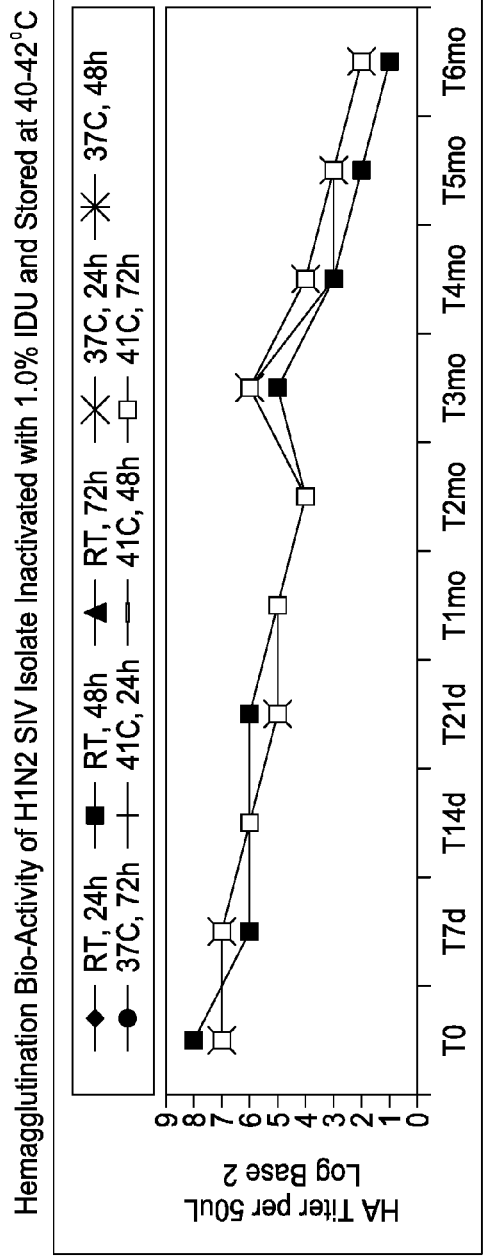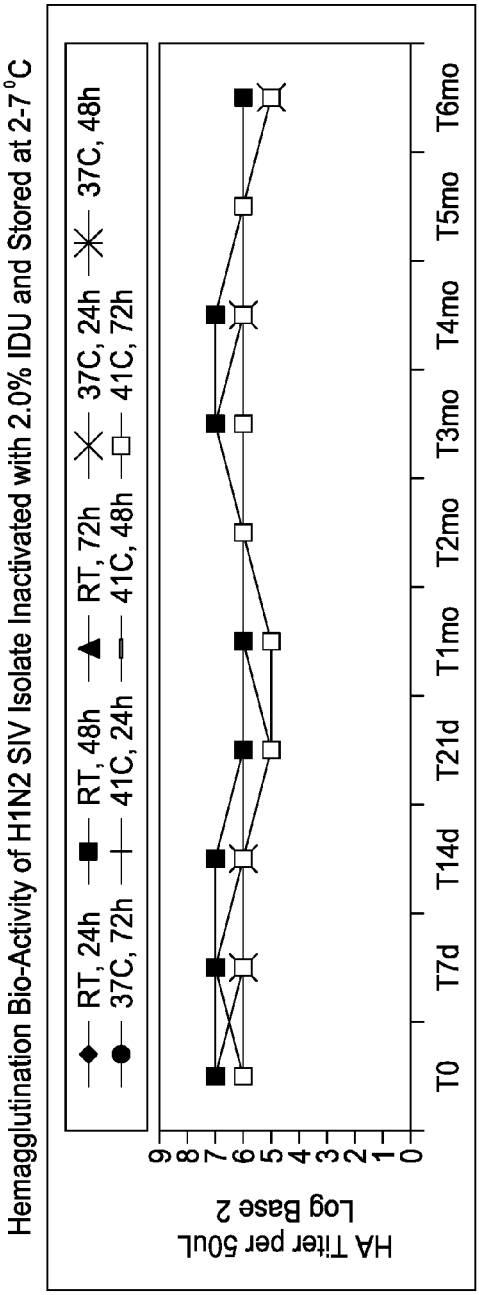

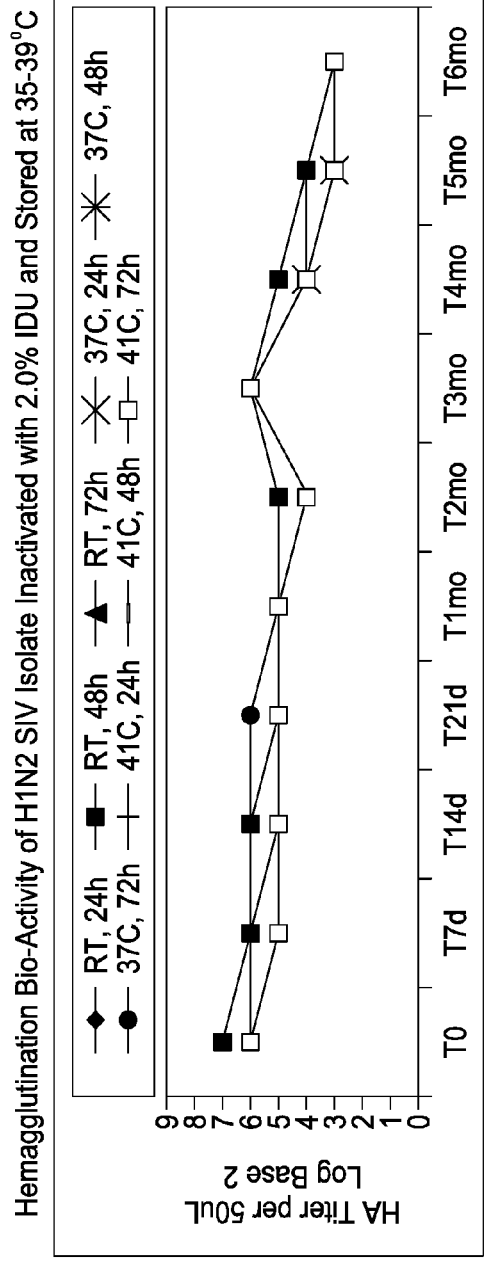
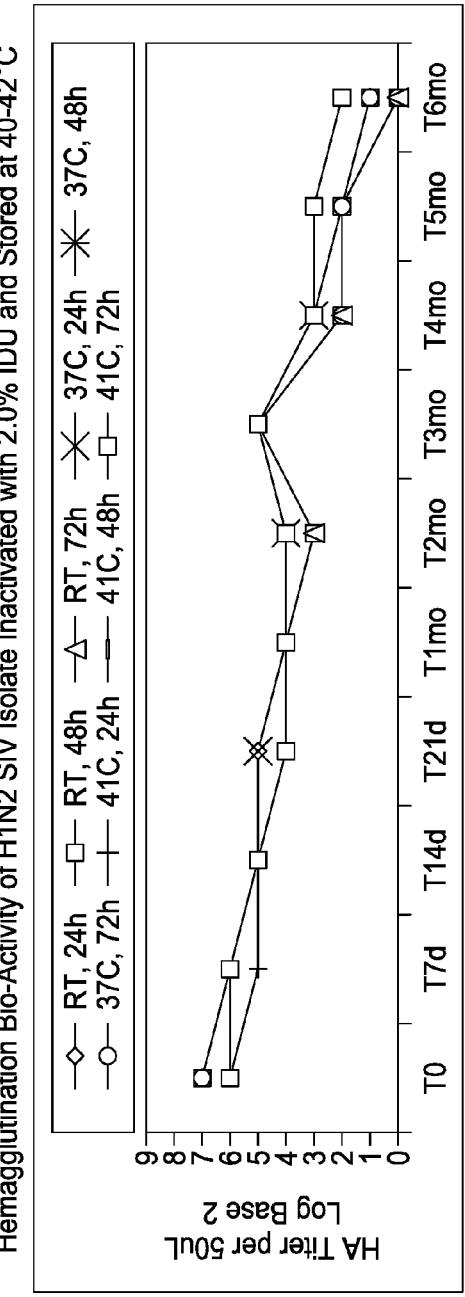

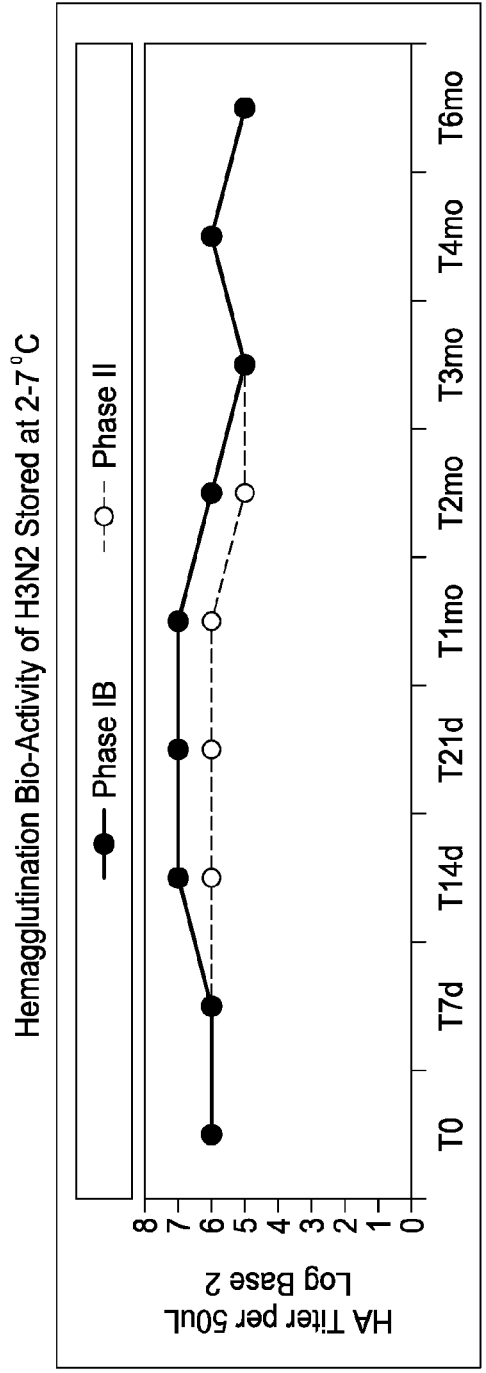
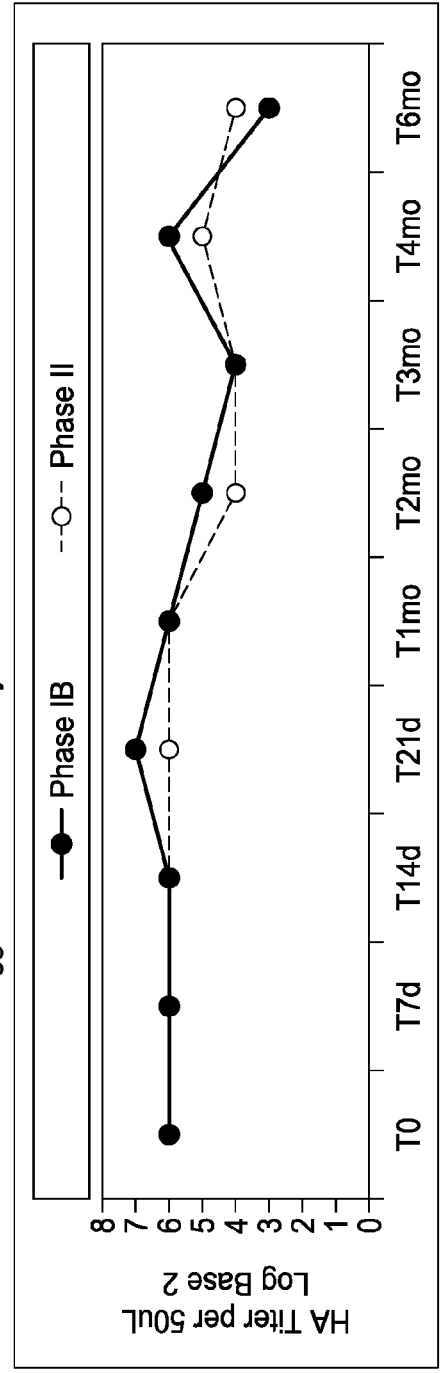
Fig-23
Fig-24

Fig-27

Hemagglutination Bio-Activity of H1N2 Stored at 35-39°C

Fig-28

Hemagglutination Bio-Activity of H1N2 Stored at 40-42°C

INACTIVATED VIRUS COMPOSITIONS AND METHODS OF PREPARING SUCH COMPOSITIONS

CLAIM OF PRIORITY

This application is a national phase filing under 35 USC § 371 from PCT Application serial number PCT/US2012/036304 filed on 3 May 2012, and claims priority therefrom. This application further claims priority from Provisional Application 61/482,367 filed 4 May 2011 both incorporated herein by reference in their entirety.

FIELD OF THE INVENTION

The present invention relates generally to inactivated swine flu virus compositions, methods of preparing such compositions, and to such compositions useful as or in vaccines. Further the present invention relates to methods of preparation, storage and transportation of precursors to and vaccine compositions wherein the precursors and vaccines can be stored and transported at ambient temperatures.

BACKGROUND OF THE INVENTION

It is known that the preparation of vaccines commonly involves the steps of inactivating a live virus (whether it be attenuated, modified or killed), so that the virus thereafter can be introduced into a living being for inducing an active immune response (e.g., a protective response) in the being. The manufacture of such vaccines often encounters any of a number of practical constraints, which create a strain on health care systems. By way of example, in recent history, shortages of influenza vaccines have been experienced due to contamination problems in the manufacturing process. In the context of viral vaccines, one approach to the manufacture of such vaccines has been to grow the specific virus in advance of preparing the vaccine composition, such as by growing the virus in chicken eggs. The manufacture of viruses according to that approach can be expensive, and time consuming, especially considering that many times, one or two eggs may be necessary to yield each dose of vaccine. One classic approach to the manufacture of vaccines has been to inactivate a virus with formalin, binary ethylenimine, formaldehyde or combinations thereof. It is also typically necessary in the manufacture of vaccines to employ one or more preservatives to help prevent contamination by bacteria, fungus or both. Among the most widely employed preservatives have been phenol, 2-phenoxyethanol, or thimerosal (which contains mercury). Concerns have been expressed as to the potential efficacy, toxicity or mutagenicity of one or more of the above agents or other ingredients of vaccines. There has been a recognized resurgence in vaccine research in recent years, which has placed an even more acute demand upon vaccine manufacturers to address the above issues.

Swine Flu Virus is a negative segmented myxovirus. It has infected a significant portion of the human population. Improved vaccines are desired. Due to its widespread affect the there is a need for widespread distribution of precursors to vaccines and vaccines for this virus. One challenge is that many precursors to vaccines and vaccines require storage and transport at low temperatures, sub ambient temperatures. Thus it presents a challenge to provide such vaccines to populations located in places that do not have infrastructure for storage and transport of such precursors at sub ambient temperatures. To prepare vaccines, viruses are inactivated so that they do not infect the host and the antigens are stabilized, so that hosts inoculated with the inactivated viruses develop immunological responses. The United States Department of Agriculture has approved protocols for using binary ethylene-imine or formaldehyde to inactivate certain viruses for vaccine production. In U.S. Pat. Nos. 5,459,073; 5,811,099; and 5,849,517, there are disclosed preservative compositions that include a formaldehyde donor agent, and specifically, one or both of diazolidinyl urea or imidazolidinyl urea. That such compositions can be used in a vaccine is addressed in U.S. Pat. Nos. 5,811,099; and 5,849,517. Commonly owned and copending U.S. application Ser. No. 12/940,112 filed Nov. 5, 2010 titled "INACTIVATED VIRUS COMPOSITIONS AND METHODS OF PREPARING SUCH COMPOSITIONS", now published as US 2011/0110975, discloses contacting a virus with a formaldehyde donor agent having a molecular weight that is greater than about 50 g/mol and less than about 400 g/mol for a period of time (e.g., at least about 12 hours) sufficient for de-activating the infectious component with the formaldehyde donor agent and for preserving at least a portion of the surface antigens to form a deactivated virus and the resulting composition. This application is incorporated herein by reference.

Notwithstanding the foregoing, there remains a need in the art for safer and less toxic inactivated live virus compositions useful in vaccines, more specifically, veterinary vaccines, and still more specifically, inactivated-viral swine vaccines, which can be produced in high yield, with inconsequential toxicity or other potential undesired side effects. What is further needed are vaccine precursors and vaccines that can be stored and transported at ambient temperatures and processes for their production, transport and storage at ambient temperatures. What is needed are compositions that can be manufactured in an efficient manner, that contain components which enhance the disinfectant and antimicrobial properties of the vaccine precursors, that exhibit hemagglutination equal to or better than industry standards, compositions that do not exhibit a loss in titer and are relatively non-toxic.

SUMMARY OF THE INVENTION

The present invention is directed at a composition comprising a live swine flu virus having an infectious component and a plurality of surface antigens on the virus in contact with a formaldehyde donor agent having a molecular weight that is less than about 400 g/mol. Preferably, the formaldehyde donor agent is selected from a non-crosslinking chemical fixative that contains urea.

The present invention provides a method for deactivating a live swine flu virus having an infectious component and a plurality of surface antigens, comprising the steps of: a) providing, a live swine flu virus having an infectious component and a plurality of surface antigens; and b) contacting the virus swine flu with a formaldehyde donor agent having a molecular weight that is greater than about 50 g/mol and less than about 400 g/mol for a period of time (e.g., at least about 12 hours) sufficient for de-activating the infectious component with the formaldehyde donor agent and for preserving at least a portion of the surface antigens to form a deactivated swine flu virus. In another embodiment, the invention is a method of preparing a composition useful as a vaccine comprising the abovementioned steps in combination with the step of c) mixing a non-toxic effective amount, for inducing an immune response in a subject to which the vaccine is administered, of the deactivated swine flu virus with a pharmaceutically acceptable carrier. Preferably the composition containing a pharmaceutically acceptable carrier is useful in, or as, a vaccine composition.

The present invention provides a method for deactivating a live virus having an infectious component and a plurality of surface antigens, comprising the steps of: a) providing a live virus having an infectious component and a plurality of surface antigens; and b) contacting the virus with a formaldehyde donor agent having a molecular weight that is greater than about 50 g/mol and less than about 400 g/mol for a period of time (e.g., at least about 12 hours) sufficient for de-activating the infectious component with the formaldehyde donor agent and for preserving at least a portion of the surface antigens to form a deactivated virus; and c) storing and/or transporting the contacted composition at ambient temperatures, that is without cold storage or transport. In another embodiment, the invention is a method of preparing a composition useful as a vaccine comprising the abovementioned steps in combination with the step of d) mixing a non-toxic effective amount, for inducing an immune response in a subject to which the vaccine is administered, of the deactivated virus with a pharmaceutically acceptable carrier. Preferably the composition containing a pharmaceutically acceptable carrier is useful in, or as, a vaccine composition.

The invention herein also contemplates vaccine compositions prepared according to the methods or using the virus of the foregoing aspects of the invention. The aspects of the present invention offer a number of advantages as compared with existing compositions useful in or as vaccines including the possibility to obtain total protection of mortality without use of an adjuvant; the ability to withstand without damaging the vaccine and/or without aggregating vaccine components after one or more freeze-thaw cycles; a reduction of cross-linking surface antigens to a significant enough degree that would result in an auto-immune hypersensitivity reaction mediated by mast cells is avoided; the vaccine protects birds from a live virus challenge (e.g., birds are given two vaccinations two weeks apart, and hemagglutination inhibition (HAI) data from samples drawn after the first vaccination indicate that a single vaccination is sufficient); a substantial reduction in the amount of antigen (e.g., a reduction by at least two logs in antigen, and more preferably at least three logs in antigen) necessary to manufacture the vaccine may be realized, a very important economic consideration. The compositions of the invention or prepared by the method of the invention facilitate storage and transportation of vaccine precursors and vaccines at ambient temperatures, that is without the need for storage and/or transportation with refrigeration. The compositions of the invention can be manufactured in an efficient manner, contain components which enhance the disinfectant and antimicrobial properties of the vaccine precursors, exhibit hemagglutination equal to or better than industry standards, do not exhibit a loss in titer and are relatively non-toxic. The invention is useful with flu antigens produced in singular or plural forms in any biological system. Such antigens may be produced in recombinant systems. In particular such antigens may be subjected to the stabilizing and efficacy treatments of the invention.

DESCRIPTION OF FIGURES

FIGS. 1 to 28 show graphs of Bio-Activity of IDU stabilized compositions over time as described in the Examples.

DETAILED DESCRIPTION

Figure 13:
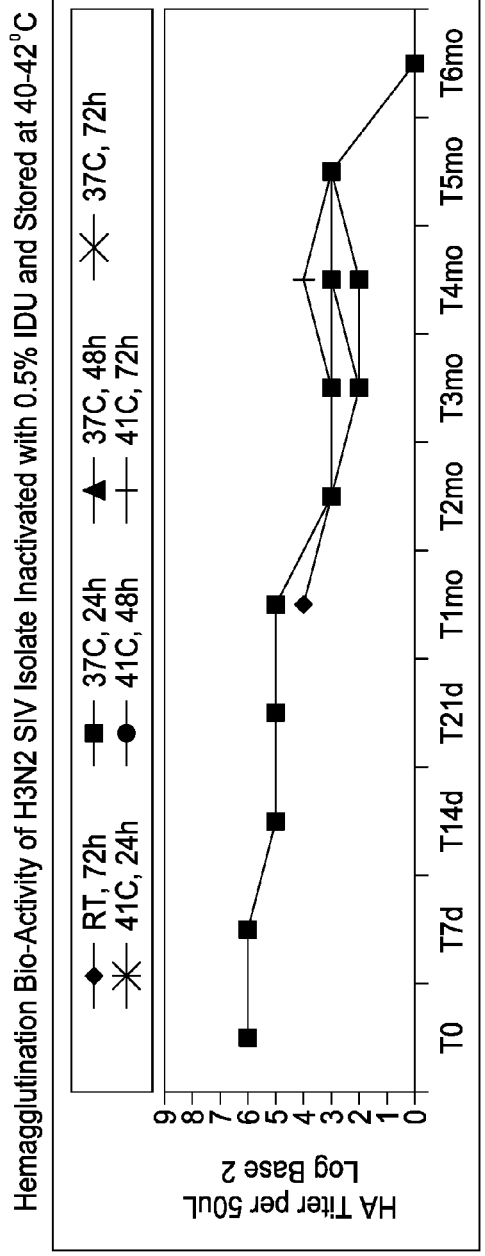

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The present invention is directed at a composition comprising a deactivated swine flu virus having an infectious component and a plurality of surface antigens in contact with a formaldehyde donor agent having a molecular weight that is less than about 400 g/mol. In addition the present invention provides an improved method for deactivating a live swine flu virus having an infectious component and a plurality of surface antigens, comprising the steps of: a) providing a live swine flu virus having an infectious component and a plurality of surface antigens; b) contacting the swine flu virus with a formaldehyde donor agent having a molecular weight that is greater than about 50 g/mol and less than about 400 g/mol for a period of time sufficient for de-activating the infectious component with the formaldehyde donor agent, and for preserving at least a portion of the surface antigens to form a deactivated swine flu virus. In another embodiment the invention is a method of preparing a composition comprising the abovementioned steps in combination with the step of c) storing or transporting the mixture at ambient temperatures. In another embodiment the invention is a method of preparing a composition comprising the abovementioned steps in combination with the step of d) mixing a non-toxic effective amount, for inducing an immune response in a subject to which the vaccine is administered, of the deactivated swine flu virus with a pharmaceutically acceptable carrier. Preferably the composition containing a pharmaceutically acceptable carrier is useful in, or as, a vaccine composition.

In another embodiment, the invention is a method comprising the steps of: a) providing a live swine flu virus having an infectious component and a plurality of surface antigens; b) contacting the swine flu virus with a formaldehyde donor agent having a molecular weight that is greater than about 50 g/mol and less than about 400 g/mol for a period of time sufficient for de-activating the infectious component with the formaldehyde donor agent, and for preserving at least a portion of the surface antigens to form a deactivated virus c) transporting or storing the contacted composition at ambient temperature.

The method for preparing a stabilized live virus composition may further comprise any one or more of the features described in this specification in any combination, including the preferences and examples listed in this specification, and includes the following features: the virus is grown in a tissue or in-vitro cell culture, such as a chicken egg; the formaldehyde donor agent is selected from a non-crosslinking chemical fixative that contains urea; the formaldehyde donor agent is selected from diazolidinyl urea (DU), imidazolidinyl urea (IDU), or a mixture thereof; the contacting step includes contacting the virus with the formaldehyde donor agent having a concentration of less than about w/v (grams per 100 ml total volume) or less; the contacting step (b) occurs for a period of about 24 to about 240 hours and more preferably about 24 to about 72 hours; the contacting step (b) occurs at a temperature of about 23° C. to about 37° C.; the method is free of any step of contacting the virus with binary ethylene-imine, formaldehyde, formatin, phenol, 2-phenoxyethanol, thimerosal, bromo-ethylene-imine, ethyl methane sulfonate, Nitrosoguanidine, fluorouracil, 5-azacytadine, or any combination thereof; the method includes a step of freeze-drying and re-hydrating the antigen-treated virus; further comprising a step of performing an assay of the deactivated virus to confirm that the infectious component has been de-activated; further comprising; c) mixing a non-toxic effective amount for inducing an immune response in a subject to which the vaccine is administered of the deactivated virus with a pharmaceutically acceptable carrier for forming a vaccine composition; the virus is an avian virus provided in a live titer amount of about $10^6$ to about $10^{12}$ EID50 per milliliter of the resulting vaccine composition; further comprising a step of contacting the virus with an adjuvant; the mixing step (c) occurs immediately following the contacting step (b); the contacted composition is transported or stored at ambient temperature; the contacted composition is transported at ambient temperature; and ambient temperature is from about 20° C. to about 37° C.

The compositions may further comprise any one or more of the features described in this specification in any combination, including the preferences and examples listed in this specification, and includes the following features: the virus manufactured by growing the virus in tissue or a chicken egg; the formaldehyde donor agent is selected from a non-crosslinking chemical fixative that contains urea; the formaldehyde donor agent is selected from diazolidinyl urea (DU), imidazolidinyl urea (IDU), or a mixture thereof; the formaldehyde donor agent is present in a concentration of less than about 1 w/v (grams per 100 ml total volume) or less; further comprising a pharmaceutically acceptable carrier or diluent; and the composition can be transported and stored at ambient temperatures.

The live virus useful in this invention is any live virus having an infectious component and a plurality of surface antigens which is capable of being deactivated for use in vaccines. Preferred live viruses are those which can be incubated in tissue or in vitro cell cultures, such as in chicken eggs. Among preferred viruses are avian flu, swine flu, bovine respiratory systhial virus and the like. In one preferred embodiment wherein the composition is transported and/or stored at ambient temperatures a preferred virus is a swine flu or an avian virus. More preferably the avian flu virus is Newcastle's disease. Still more specifically, the virus is a strain of Newcastle Disease Virus selected from a lentogenic strain, a mesogenic strain, a velogenic strain or any combination thereof. For example, the virus is a La Sota strain (e.g., Mass. type) of Newcastle Disease Virus.

The amount of time for the contacting step preferably is sufficient for de-activating the virus (whether by attenuating it, modifying it or killing it), while sufficiently preserving surface antigens so that when a subject is vaccinated with a vaccine composition including the deactivated virus, the deactivated virus will induce an immunity response (e.g., a response that is measurable by Hemagglutination Inhibition Assay, such that the response allows the vaccinated subjects to survive exposure to a lethal dosage of the live virus). In a preferred embodiment, the contacting occurs for a period of time of about 12 hours or greater and more preferably about 24 hours or greater. In a preferred embodiment, the contacting occurs for a period of time of about 240 hours or less, more preferably 120 hours or less, even more preferably about 72 hours or less, and most preferably about 48 hours or less. In a preferred embodiment, the contacting step occurs at a temperature of about 20° C. or greater, more preferably about 23° C. or greater and most preferably about 25° C. or greater. In a preferred embodiment, the contacting step occurs at a temperature of about 37° C. or less, more preferably about 30° C. or less; and most preferably about 25 C or less.

The viral infection that is useful in the teachings herein preferably is a swine flu virus. More specifically, the virus is a strain of Swine Flu Virus is selected from those designated H1N1, H1N2, H3N2 or the like. When the virus is used in a composition used as a vaccine it is provided in a sufficient amount for invoking an immunity response in a subject to which the vaccines herein are administered. By way of example, the swine fluid virus may be provided in a live titer amount of about $10^3$ to about $10^{12}$ titer per milliliter of the resulting vaccine composition and more preferably about $10^6$ to about $10^{11}$ titer per milliliter of the resulting vaccine composition. More specifically, the virus titer may range from about $10^6$ to about $10^8$ titer per milliliter of the resulting vaccine composition. By way of example, the avian virus may be provided in a live titer amount of about $10^6$ to about $10^{11}$ titer per milliliter of the resulting vaccine composition. The formaldehyde donor agent is selected from a non-crosslinking chemical fixative that contains urea. More preferably, the formaldehyde donor agent is selected from diazolidinyl urea (DU), imidazolidinyl urea (IDU), or a mixture thereof. The formaldehyde donor agent may consist essentially of diazolidinyl urea (DU) imidazolidinyl urea (IDU), or a mixture thereof.

In the embodiment wherein the virus is an avian flu, the contacting step generally includes contacting the virus with the formaldehyde donor agent having a concentration of about 5 w/v (grams per 100 ml total volume) or less and more preferably about 4 w/v or less. Preferably, the formaldehyde donor agent may be present in a concentration of about 5 w/v (grams per 100 ml total volume) or greater and more preferably about 1 w/v (grams per 100 ml total volume) or greater. In the embodiment wherein the virus is a swine flu virus, the contacting step generally includes contacting the virus with the formaldehyde donor agent having a concentration of about 1 w/v (grams per 100 ml total volume) or less and more preferably about 0.5 w/v or less. Preferably, the formaldehyde donor agent may be present in a concentration of about 0.0625 w/v (grams per 100 ml total volume) or greater and more preferably about 0.1 w/v (grams per 100 ml total volume) or greater. The contacting step may be the only step during which the live virus is contacted with the formaldehyde donor agent.

The mixing step is a step that can be employed for preparing the resulting composition useful as a vaccine. The mixing step may occur immediately following the contacting step (such that there is no intermediate washing, quenching step or other step by which the deactivated virus would be subjected to a fluid other than a carrier of the vaccine composition), or it may occur during the time period when the contacting step (b) is occurring. Thus, it will be appreciated that during the mixing step the deactivated virus will remain in contact with solution that includes the formaldehyde donor agent. During the mixing step, the antigen-treated virus may be maintained at a temperature above about 15° C. (e.g., it may be about room temperature).

The composition of the invention generally will thus include a pharmaceutically acceptable carrier or diluent, which may be a liquid, a solid, a gel or otherwise. By way of illustration, the antigen-treated virus may be admixed in a suitable carrier (e.g., one based on a water or a saline solution) that optionally is buffered (e.g., phosphate buffered saline, such as Dulbecco's phosphate buffered saline "D-PBS") before administering into a subject animal. Preferably, the carrier is such that the antigen-treated virus is uniformly dispersed in the resulting composition at the time of the administration, and it will not degrade the antigen-treated virus throughout a storage life of at least 10 days, more preferably at least one month at a temperature of about 0° C. to about 37° C. An example of one suitable solution includes a mixture of $CaCl_2$ (Calcium Chloride); $MgCl_2$ (Magnesium Chloride); KCl (Potassium Chloride); $KH_2PO_4$ (Potassium Phosphate, monobasic); NaCl (Sodium Chloride); $Na_2HPO_4$ (Sodium Phosphate, dibasic); and DGlucose (dextrose). More specifically, one example of such a solution is set forth in the following Table 1, where mM refers to milli-molarity; millimoles/liter.

TABLE I

| | |
|---|---|
| $CaCl_2$ | 0.901 mM |
| $MgCl_2$ | 0.493 mM |
| KCl | 2.67 mM |
| $KH_2PO_4$ | 1.47 mM |
| NaCl | 137.93 mM |
| $Na_2HPO_4$ | 8.06 mM |
| D-Glucose | 5.56 mM |

As taught in U.S. Pat. No. 7,252,984, a carrier or diluent may include one or any combination of stabilizers, preservatives and buffers. Suitable stabilizers may include, for example SPGA, carbohydrates (such as sorbitol, mannitol, starch, sucrose, peptone, arginine, dextran, glutamate or glucose), proteins (such as dried milk serum, albumin or casein) or degradation products thereof. Suitable buffers may include for example alkali metal phosphates. Suitable preservatives may include thimerosal, merthuilate and gentamicin. Diluents include water, aqueous buffer (such as buffered saline) and polyols (such as glycerol). It will be appreciated that vaccine compositions herein, as well as any of its carrier or diluents is preferably free of any anti-biotic, and/or any mercury-containing ingredient.

The method may further comprise a step of contacting the virus with an adjuvant. Any suitable adjuvant may be utilized in the compositions and methods of this invention. Exemplary adjuvants include those selected from one or any combination of lecithin, a pharmaceutically acceptable polymer, saponin or a derivative thereof, cholesterol, aluminium hydroxide, -phosphate or -oxide, oil-in-water or water-in-oil emulsion based on, for example a mineral oil, a vegetable oil (such as vitamin E acetate), or some other suitable carboxylic acid. See, e.g., U.S. Pat. No. 5,152,981, incorporated by reference. If an adjuvant is employed, it may be employed in a suitable amount for providing adjuvant activity. Thus, by way of example, following treatment of the surface antigens of the virus, the deactivated virus may diluted into D-PBS, which may include an adjuvant or be free of an adjuvant. Other examples of suitable adjuvants may include one or any combination of compounds or compositions for this purpose The composition and method for making it is a relatively simple and elegant to a technology that previously has seen various potentially complicating approaches. Though such approaches may be employed with the teachings herein, it is preferable that the vaccine composition and the virus are free of any contact with any plant-cell-produced components: the virus includes or is free of an infectious genetically engineered, genetically modified or cloned virus; the method may optionally be free of any step of contacting the virus with binary ethylene-imine, formaldehyde, formalin, phenol, 2-phenoxyethanol, thimerosal, bromo-ethylene-imine, ethyl methane sulfonate, nitrosoguanidine, fluorouracil, 5-azacytadine, or any combination thereof; or any combination of the foregoing. It is also possible that the vaccine composition may include or be free of any neutralizing antibodies bound to the surface antigens. It is also possible that the vaccine composition may otherwise include or be free of an antioxidant.

Other variations of the invention are also possible. To illustrate, the method may include a step of freeze-drying and re-hydrating the antigen-treated virus. The antigen-treated virus may include or be free of any temperature reduction to a temperature below about 10° C. (e.g., to below about 0° C.). The method may include or be free of any step that removes the formaldehyde donor agent prior to the mixing step. Accordingly, the various aspects of the invention contemplate that the administration of the vaccine composition is accomplished in the absence of any step of diluting the composition at the time of or at the site of administration of the vaccination. The mixing step described previously could constitute the only diluting step that occurs in the methods herein. The method may also include one or more steps of storing the resulting composition for a period of at least 30 days, at least 60 days, or even at least 90 days following the mixing step; storing the resulting composition at one or more temperatures of below about 1 St (e.g., about 0 to about 10° C.), with the composition retaining its stability under such conditions (e.g., the amount of useful deactivated virus remains within about 20% and more preferably within about 10% of the titer amount at the time of the mixing step). The composition may be stored in suitable sealed containers, such as stopped vials (e.g., rubber stopped glass or plastic vials), sealed syringes, blister packaging, or otherwise. Preferably the method includes storing or transporting any composition of the invention or prepared by the methods of the invention at ambient temperature, wherein ambient temperature is defined hereinbefore. When such compositions are stored or transported at ambient temperatures such compositions retain their efficacy as described hereinbefore.

The method may also include one or more steps of performing an assay of the deactivated virus to confirm that the infectious component has been de-activated. The methods herein further contemplate immunizing a subject with a vaccine composition prepared according to the present teachings. Thus the methods herein may further comprise at least one step of administering a subject in need of immunization with the vaccine composition described in the present teachings. Any step of administering a subject in need of immunization with the vaccine composition by performed by ingestion (e.g., from drinking water), intranasally (e.g., by aerosol), intraocularly (e.g., by aerosol), via intramuscular injection, by subcutaneous injection, by delivering into eggs prior to hatching (e.g., manually or by machine); or any combination thereof. A plurality of steps of administering the vaccine to the subject may be performed at intervals (e.g., they may be administered to the same subject on multiple occasions, such as at intervals of at least 3 days). By way of further example, at least two steps of administering the subject may performed at intervals of greater than one week (e.g., about 14 days apart). It is also possible that only a single dose is administered and is sufficient for achieving the desired satisfactory immune response.

As gathered from the foregoing, another aspect of the present invention is directed at deactivated virus described herein that has been contacted with a formaldehyde donor agent according to the above teachings, as well as compositions useful as vaccines (including the and one or more of the other ingredients, e.g., one or more of a carrier, an adjuvant, or both) resulting from the methods herein. Resulting viruses treated according to the teachings herein may be characterized as being free of cross-linking with other surface antigens of the virus.

The dosage of the vaccine preferably will be a sufficient amount for inducing immunity in the vaccinated subjects against challenge by a virulent form of the virus, wherein immunity can be described as the realization within a period of 4, days, more preferably 7 days, and still more preferably 14 days after challenge of a death rate due to the virulent form of the virus that is less than 50% of the population of subjects challenged, more preferably less than 25% of subjects challenged and still more preferably less than 5% of subjects challenged (e.g., approximately 100% of challenged subjects survive the challenge). Challenges include the step of administering the virulent form of the virus to the subject in a 100% lethal dosage amount.

Though illustrated in connection with immunization for prevention of swine flu virus, the present invention is not intended to be so limited. It may have application for immunization for prevention of other viruses, including but not limited to other avian paramyxoviruses, avian influenza (e.g., H5 or H7 influenza, such as H5N1 influenza), avian polyoma virus, Pacheco's disease, West Nile Virus, diminuvirus, chicken anemia virus, or Circo virus. The vaccine compositions herein may also include a plurality of antigenic components suitable for immunizing against a plurality of viruses. For example, the invention contemplates that the resulting vaccine may immunize against Swine Flu Virus and one or more other viruses. The methods and compositions herein may be employed in the immunization of mammal and avian subjects.

The method of the invention comprises the steps of: providing a live virus having an infectious component and a plurality of surface antigens; b) contacting the virus with a formaldehyde donor agent having a molecular weight that is greater than about 50 g/mol and less than about 400 g/mol for a period of time sufficient for de-activating the infectious component with the formaldehyde donor agent, and for preserving at least a portion of the surface antigens to form a deactivated virus. The method of the invention may further comprise one or more of the following features in any combination. The virus is grown in a chicken egg; the virus is Swine flu virus; the formaldehyde donor agent is selected from, or consists essentially of, a non-crosslinking chemical fixative that contains urea. The formaldehyde donor agent is selected from, or consists essentially of, diazolidinyl urea (DU), imidazolidinyl urea (IDU), or a mixture thereof. The resulting solution consists essentially of de-activated virus and the formaldehyde donor agent; the contacting step includes contacting the virus with the formaldehyde donor agent having a concentration of less than about 1 w/v (grams per 100 ml total volume) or less, preferably about 0.5 w/v or less (grams per 100 ml total volume) and preferably about 0.625 w/v (grams per 100 ml total volume or greater), and more preferably about of about 0.1 w/v (grams per 100 ml total volume) or greater. The contacting step (b) occurs for a period of about 24 to about 72 hours. The contacting step (b) occurs at a temperature of about 20° C. to about 37° C., preferably about 25° C. The mixing step (c) occurs immediately following the contacting step (b). During the time period throughout the contacting step (b) the antigen-treated virus is maintained at a temperature of about 20° C. or greater. The contacting step (b) is the only step during which the live virus is contacted with the formaldehyde donor agent. The resulting composition may be free of any contact with any plant-cell-produced components. The virus includes an infectious genetically engineered, genetically modified or cloned virus. The virus may be free of any infectious genetically engineered, genetically modified or cloned virus. The method may be free of any step of contacting the virus with binary ethylene-imine, formaldehyde, formalin, phenol, 2-phenoxyethanol, thimerosal, bromo-ethylene-imine, ethyl methane sulfonate, Nitrosoguanidine, fluorouracil, 5-azacytadine, or any combination thereof. The method may include a step of freeze-drying and re-hydrating the antigen-treated virus. The method may further comprise a step of performing an assay of the deactivated virus to confirm that the infectious component has been de-activated. The method may be free of any step of reducing the temperature of the virus to below about 20° C. The surface antigens may be free of cross-linking with other surface antigens of the virus. The method may further comprise; c) mixing a non-toxic effective amount for inducing an immune response in a subject to which the vaccine is administered of the deactivated virus with a pharmaceutically acceptable carrier for forming a vaccine composition. The virus is an avian virus provided in a live titer amount of about $10^8$ to about $10^{11}$ Eid per milliliter of the resulting vaccine composition. The method may further comprise a step of contacting the virus with an adjuvant. The mixing step (c) may occur immediately following the contacting step (b); during the time period throughout the contacting step (b) and the mixing step (c). The antigen-treated virus is maintained at a temperature of about 20° C. During the time period throughout the contacting step (b) and the mixing step (c), the antigen-treated virus may be free of any temperature reduction to a temperature below about 20° C. The method may be free of any step that removes the formaldehyde donor agent prior to the mixing step (c). The composition of the invention comprises a deactivated virus having an infectious component and a plurality of surface antigens in contact with a formaldehyde donor agent having a molecular weight that is less than about 400 g/mol. The composition of the invention may further comprise one or more of the following features in any combination. The formaldehyde donor agent is selected from, consists essentially of, a non-crosslinking chemical fixative that contains urea. The formaldehyde donor agent is selected from, consists essentially of, diazolidinyl urea (DU), imidazolidinyl urea (IDU), or a mixture thereof. The formaldehyde donor agent is present in a concentration of about 1 w/v (grams per 100 ml total volume) or less and more preferably about 0.5 w/v (grams per 100 ml total volume) or less and about 0.625 w/v (grams per 100 ml total volume) or greater and more preferably about 0.1 (grams per 100 ml total volume) or greater. The composition further comprises a pharmaceutically acceptable carrier or diluent. The resulting composition may be free of any contact with any plant-cell-produced components. The virus may include an infectious genetically engineered, genetically modified or cloned virus; the virus is free of any infectious genetically engineered, genetically modified or cloned virus. The composition may be free of binary ethylene-imine, formaldehyde, formalin, phenol, 2-phenoxyethanol, thimerosal, bromo-ethylene-imine, ethyl methane sulfonate, Nitrosoguanidine, fluorouracil, 5-azacytadine, or any combination thereof. The surface antigens may be free of cross-linking with other surface antigens of the virus. A non-toxic effective amount for inducing an immune response in a subject to which the vaccine of the deactivated virus of a pharmaceutically acceptable carrier is administered. The virus may be an avian virus provided in a live titer amount of about $10^6$ to about $10^{11}$ $EID_{50}$ per milliliter. The composition retains its immunological efficacy after storage and transportation at ambient temperature, about 20° C. to about 37° C. and more preferably about 23° C. to about 30° C.

Illustrative Embodiments of the Invention

The following examples are provided to illustrate the invention, but are not intended to limit the scope thereof. All parts and percentages are by weight unless otherwise indicated.
Test Methods
Inactivation Sample Hemagglutination Assay (HA) is run to determine if inactivation treatment degrades virus surface epitopes necessary for hemagglutination. If so, the HA result should be negative. The desired result is positive hemagglutination, thereby confirming that surface epitopes are preserved. More specifically, in this assay, a sample is incubated with a fresh preparation of chicken red blood cells (cRBC5). Hemagglutination (HA) is defined as the clumping of cRBCs. The virus can promote hemagglutination through the interaction of molecules on the virus surface with molecules on the surface of cRBC5. Damaged or degraded virus does not promote hemagglutination. Depending on the sample used (treated/untreated virus or allantoic fluid—AF—from inoculated eggs), the results may be interpreted differently. If the sample is treated/untreated virus (the inactivation sample), a positive HA result indicates that the virus is not degraded due to the treatment—it gives no information (in this case) about the viability of the virus (inactivation state). If the sample is the allantoic fluid from an inoculated egg, a positive HA result indicates that the virus is not inactivated by the treatment (the virus was active and able to replicate in the egg). If the virus is completely inactivated by the treatment (eg—incubation with DU/IDU/BEI/formaldehyde), the small amount of virus in the inoculum would be diluted out by the large volume of AF, and the HA result would be negative.

Embryonic Toxicity assay is run to determine if the virus is still viable after the inactivation treatment. If still viable the virus would replicate in allantoic fluid and kill an embryo to which it is contacted. The desired result is embryonic viability, thereby confirming the presence of no live virus. More specifically, embryonic toxicity is assessed by candling the eggs, such that an egg is placed on a source of bright light (e.g. a flashlight), and the embryo is directly observed. Viable embryos are identified by certain visual cues (pulsatile vasculature, for example). In these experiments, embryonic death may be due to one of three things: (1) injury/infection resulting from the needle stick used in the injection; (2) chemical toxicity (by inactivating agent—DU/IDU); or (3) live virus replication (as a result of incomplete NDV inactivation).

Allantoic fluid (AF: from injected eggs) HA Assay is run to determine if the virus is not viable. If not viable, inactivated virus would not replicate and injected virus would be diluted out in AF. If, after 'inactivation' treatment, the virus is still viable, allantoic fluid would contain high enough titer of virus to promote hemagglutination. The desired result is negative hemagglutination, thereby confirming that the AF fluid contains no live virus.

Chicken Embryonic Fibroblast (CEF) Immunofluorescence (IF) Assay is run to determine whether successful inactivation occurs. It is recognized that chicken embryonic fibroblasts (CEF) grow well in culture and are highly susceptible to infection by liveSwine Flu. In this assay, allantoic fluid (AF) from inoculated eggs is applied to confluent CEF monolayers. After 5 days, cells are washed, fixed and stained with anti-viral antibodies. Positive staining indicates that there was live virus in AF, and therefore, 'inactivation' treatment is unsuccessful. The desired result is no staining (which indicates that the virus had been completely inactivated), and supports that the AF fluid contains no live virus.

Hemagglutination Inhibition Assay is run with serum samples obtained from vaccinated and/or control animals are incubated with live virus prior to use in the aforementioned HA assay. If the cRBCs do not agglutinate (negative result), the conclusion is that there were specific anti-viral antibodies in the serum (seroconversion) which blocked the viral antigens from interacting with the cRBCs. A serum HAI titer of greater than 16 correlates with an animal successfully rejecting a subsequent live viral challenge. An example of one such assay is found in Allan and Gough, "A standard haemagglutination inhibition test for Newcastle disease. (2) Vaccination and Challenge". Vet Rec., Vol. 95, Issue 7, 147-149, Aug. 17, 1974.
Test Results
Testing is performed on Swine influenza virus (SIV) H1N1. The virus is characterized in red blood cells (RBC) a permissive cell type for assaying the hemagglutination (HA) activity and cytopathic effect (CPE) is identified. Imidazolidinyl urea preparations are prepared in Dulbecco's phosphate buffered saline at concentrations as described hereinafter. Equal volumes of virus are mixed with the imidazolidinyl urea. The resulting solutions are then serially diluted and added to cell monolayers. The plates are incubated at 37° C., in 5% carbon dioxide for 5 to 6 days. The monolayers are observed for morphological changes associated with cytotoxicity effect (CTE) or CPE caused by imidazolidinyl urea and Swine Influenza Virus.

Concentrations of 0.0625, 0.1250, 0.250 and 0.500 of imidazolidinyl urea (IDU) are tested according to the protocol described. The results are compiled in Table 2.

TABLE 2

| Example | IDU Conc % | HA Titer per ml SIV Present | CTE Titer per ml SIV Present | CTE Titer per ml No SIV | CPE Titer per ml above (above CTE titer) SIV Present |
|---|---|---|---|---|---|
| 1 | 0.5000 | 1920 | 1280 | 1280 | 40 |
| 2 | 0.2500 | 1920 | 1280 | 1280 | 0 |
| 3 | 0.1250 | 1920 | 640 | 640 | 0 |
| 4 | 0.0625 | 1920 | 160 | 160 | 80 |
| 5 | 0 | 1280 | | | 40960 |

The data demonstrates that imidazolidinyl urea levels of 0.0625, 01250, 0.2500 and 0.5000 levels significantly reduce SIV infectivity with incubations of 37° C. for 18 hours.

The inactivation of SIV infectivity using imidazolidinyl urea, BEI and an untreated SIV control is studied. The virus is prepared as described hereinbefore. The virus is expanded to a total of 350 ml and the infectivity and HA bioactivity is determined as approximately 8.00 TCID$_{50}$/ml and 1280 HA/ml. Infectivity is determined using a MDCK cell line and microscopic observations for cytopathic effects as the 50 percent end point. Complete inactivation is tested using fluorescent antibody to type A influenza. The HA bioassay is performed using chicken red blood cells that are observed and scored for hemaglutination. Three treatment groups are prepared, IDU treated, BEI treated and untreated. Each preparation is incubated at room temperature for approximately 72 hours with continuous rocking. After incubation, infectivity and HA bioactivity are tested using MDCK and chicken red blood cells, respectively. Each preparation is aloquoted into four volumes and placed at 2-7° C., 22-25° C., 35-38° C., and 40-42° C. Samples are collected at 0 days, 7 days, 14 days, 21 days, 1 month, 3 months, 6 months and 12 months. the HA bioactivity is tested on the day of collection at each time point. A 3 percent BEI solution is prepared and 4.5 ml is mixed with 150 ml of virus lysate. A 10 percent stock of imidazolidinyl urea is prepared in sterile RO/DI water and filter stabilized. A 0.5 percent imidazolidinyl urea concentration a 7.5 ml portion of the e10 percent stock is mixed with 150 ml of virus lysate. Infectious titers of the base samples are determined for the untreated version as 8.00 TCID$_{50}$/ml and 8.50 FAID$_{50}$/ml. For BEI treated and IDU treated samples, the results are below the level of detection, where the level of detection is ≥1.3 TCID$_{50}$/ml and 1.3 FAID$_{50}$/ml.

The results of the Hemagglutination bio-activity is compiled in Table 3.

twenty-one months. The HA bio-activity was retained in all samples tested following inactivation. The HA bio-activity of samples stored at 2-7° C. fluctuated between titers of 7 and 8 during the twenty-one months of incubation. The only exception was month six in which all samples had a titer of 6. The results are graphed in FIG. 1. The HA bio-activity of the untreated and IDU-inactivated viruses stored at 22-25° C. fluctuated between titers of 6-8 through the fifteen months of incubation, then decreased to a titer of 4 after twenty-one months of incubation. The HA bio-activity of the BEI-inactivated virus stored at 22-25° C. fluctuated between titers of 7 and 8 through the first three and a half months of incubation, then was undetectable (titer of <2) after twenty-one months of incubation. The results are graphed in FIG. 2. In the first phase of testing, there was no real difference in HA bio-activity between any of the H1N1 isolate treatments stored at 2-7° C. for up to twenty-one months following inactivation. The H1N1 isolate inactivated with IDU demonstrated at least a retention of 3 to 4-fold greater amount of HA bio-activity compared to the BEI inactivated virus from fifteen months through twenty-one months of incubation at 22-25° C. The HA bio-activity of all Phase I samples collected during the first fifteen months of incubation were tested using one lot of cRBC. The HA bio-activity titers for all samples were within 2 logs of the original titer obtained on the day of collection. The only exception is the untreated virus stored, at 40-42° C. at three and three and a half months which had titers that were 3 and 4 logs higher, respectively, than those obtained on the original days of collection (see Table 4).

TABLE 3

| Sample type | T ° C. | Time Days 0 | Time Days 7 | Time Days 14 | Time Days 21 | Time Months 1 | Time Months 3 | Time Months 3.5 | Time Months 6 | Time Months 12 |
|---|---|---|---|---|---|---|---|---|---|---|
| SIV | 2-7 | 128 | 128 | 256 | 128 | 128 | 128 | 128 | 64 | 256 |
| SIV | 22-25 | | 128 | 256 | 128 | 128 | 128 | 128 | 64 | 128 |
| SIV | 35-38 | | 128 | 256 | 128 | 128 | 4 | 4 | <2 | 16 |
| SIV | 40-42 | | 128 | 128 | 32 | 16 | 2 | 2 | ND | ND |
| BEI | 2-7 | 256 | 128 | 256 | 128 | 128 | 128 | 128 | 64 | 128 |
| BEI | 22-25 | | 128 | 256 | 128 | 128 | 128 | 128 | 16 | 32 |
| BEI | 35-38 | | 128 | 128 | 64 | 64 | 64 | 64 | 2 | 4 |
| BEI | 40-42 | | 128 | 64 | 4 | <2 | 2 | 2 | ND | ND |
| IDU | 2-7 | 256 | 128 | 256 | 128 | 128 | 128 | 128 | 64 | 64 |
| IDU | 22-25 | | 128 | 256 | 128 | 128 | 128 | 128 | 64 | 4 |
| IDU | 35-38 | | 256 | 256 | 128 | 128 | 32 | 16 | <2 | ND |
| IDU | 40-42 | | 128 | 256 | 128 | 32 | 2 | 2 | ND | 64 |
| SIV[1] | | 256 | 256 | 256 | 128 | 128 | 128 | 128 | 128 | 128 |

[1]No incubation

Inactivation Studies

H1N1 virus was inactivated using 0.5% IDU or 3% v/v BEI at room temperature for 72 hours. Preparations of each sample were placed at 2-7° C., 22-25° C. 35-39° C. and 40-42° C. for the forced degradation assay. Samples were collected and tested for HA bio-activity every week for the first month, at three months, three and a half months, six months, twelve months, fifteen months, eighteen months and twenty-one months. After three and a half months the testing of all samples being stored at 40-42° C. was discontinued due to loss of detectable HA bio-activity. After twelve months, the testing of all samples stored at 35-39° C. was discontinued due to loss of detectable HA bio-activity.

Additional HA bio-activity has been tested on the H1N1 isolate stored at 2-7° C. and 22-25° C. at fifteen months, eighteen months and twenty-one months. All samples collected to date have been tested for HA bio-activity using cRBC. The positive control viruses (H1N1 or H1N2 isolates, not-inactivated) had HA titers of 6-8 (log base 2) during the Phase 2 Testing The purpose of Phase II of this project was to extend the HA bio-activity testing of the H1N2 virus and H3N2 virus from three months to one year. The H1N2 and H3N2 viruses were inactivated using IDU and BEI. The H1N2 and H3N2 viruses were inactivated with 0.5% IDU and 3% v/v BEI at room temperature for 72 hours. The untreated virus samples were retained at 2-7° C. until the initiation of the forced degradation assay. Preparations of each sample were placed at 2-7° C., 22-25° C., 35-39° C. and 40-42° C. for the forced degradation assay. Samples were collected and tested for HA bio-activity on days three, seven, ten, fourteen, and twenty-one; one month, two months, three months, four months, six months, nine months and twelve months. After the four month testing date all samples being incubated at 40-42° C. were no longer tested due to a loss of detectable HA bio-activity.

Treatment of the H1N2 and H3N2 SIV isolates with 0.5% IDU and 3% v/v BEI for 72 hours resulted in complete SIV infection inactivation (≤1.5 TCID$_{50}$/ml). No cytopathic effect was observed in indicator cells. As expected, there was a minimal cytotoxic effect due to the IDU. The H1N2 SIV virus yielded a titer of 5.8 TCID$_{50}$/ml before inactivation and the H1N2 positive control virus yielded a titer of 6.8 TCID$_{50}$/ml. The H3N2 SIV virus yielded a titer of 4.8 TCID$_{50}$/ml before inactivation and the H3N2 positive control virus yielded a titer of 6.0 TCID$_{50}$/ml.

The HA bio-activity was tested on days three, seven, ten, fourteen, and twenty-one; one month, two months, three months, four months, six months, nine months and twelve months. All samples collected to date were tested for HA bio-activity using cRBC. The H1N2 positive control has had an HA titer of 6-7 and the H3N2 positive control has had an HA titer of 5-7 during the twelve months. The HA bio-activity was retained in all samples tested following inactivation. The HA bio-activity of the untreated and BEI-inactivated H1N2 viruses stored at 2-7° C. fluctuated between titers of 6 and 7 through twelve months of incubation. The HA bio-activity of the IDU-inactivated H1N2 viruses stored at 2-7° C. fluctuated between titers of 6 and 7 through the first two months of incubation then decreased to a titer 4 after twelve months, see FIG. 3. The HA bio-activity of the untreated and BEI-inactivated H1N2 viruses stored at 22-25° C. fluctuated between titers of 6 and 7 through twelve months of incubation. The HA bio-activity of the IDU-inactivated H1N2 viruses stored at 22-25° C. retained a titer of 6 through the first twenty-one days of incubation, then decreased to a titer of 2 after twelve months see FIG. 4. The HA bio-activity of the untreated and BEI-inactivated H1N2 viruses stored at 35-39° C. fluctuated between titers of 6 and 7 through the first month of incubation, then was undetected (titer of <2) after three months. The HA bio-activity of the IDU-inactivated H1N2 viruses stored at 35-39° C. retained a titer of 6 for the first three days, retained a titer of 4 through fourteen days and then gradually decreased below the level of detection to a titer of <2 after three months. The titer for the untreated virus increased to a titer of 1 after nine months, then below the level of detection to a titer of <2 at twelve months. The titer for the IDU-inactivated virus increased during the six to twelve month testing period see FIG. 5. The HA bio-activity of the untreated and BEI-inactivated H1N2 viruses stored at 40-42° C. retained a titer of 6 for the first three days of incubation. The HA bio-activity of the BEI inactivated H1N2 virus decreased below the level of detection after fourteen days, then had a low level of activity at one month. The HA bio-activity of the untreated and IDU inactivated H1N2 viruses decreased below the level of detection after 1 month, see FIG. 6.

The H1N2 virus inactivated with BEI maintained similar HA bio-activity as the untreated H1N2 virus at the 2-7° C., 22-25° C. and 35-39° C. storage temperatures. The HA bio-activity of the BEI inactivated H1N2 virus decreased more rapidly than the untreated virus at 40-42° C. The HA bio-activity of the H1N2 virus inactivated with IDU decreased at a greater rate at every storage temperature, than the untreated or BEI inactivated viruses. The HA bio-activity of the untreated and BEI-inactivated H3N2 viruses stored at 2-7° C. fluctuated between titers of 6 and 7 through twelve months of incubation. The HA bio-activity of the IDU-inactivated H3N2 viruses stored at 2-7° C. fluctuated between titers of 6 and 7 through the first two months of incubation then between titers of 5, and 6 through twelve months, see FIG. 7. The HA bio-activity of the untreated and BEI-inactivated H3N2 viruses stored at 22-25° C. fluctuated between titers of 6 and 7 through twelve months of incubation. The HA bio-activity of the IDU-inactivated H3N2 viruses stored at 22-25° C. fluctuated between titers of 6 and 7 through the first two months of incubation, then between titers 5 and 7 through twelve months, see FIG. 8. The HA bio-activity of the untreated H3N2 virus stored at 35-39° C. fluctuated between titers of 5 and 6 through the first four months of incubation, then decreased to a titer of 4 after twelve months. The HA bio-activity of the BEI-inactivated and the IDU-inactivated H3N2 viruses stored at 35-39° C. fluctuated between titers of 5 and 7 for the first two months, then between titers of 3 and 6 through nine months of incubation. After twelve months of incubation the BEI-inactivated H3N2 virus retained a titer of 3, whereas the IDU-inactivated H3N2 virus IHA bio-activity was not detected (titer <2), see FIG. 9. The HA bio-activity of the BEI-inactivated H3N2 virus stored at 40-42° C. was below the level of detection (titer of <2) after seven days and fluctuated between a below the level of detection and 2 through four months. The HA bio-activity of the untreated H3N2 virus fluctuated between a titer of 2 or 3 throughout one month, then was not detected two months. The HA bio-activity of the IDU-inactivated H3N2 virus started with a titer of 6 and retained a titer of 5 through the first month of incubation. After two months the IDU-inactivated H3N2 virus had a titer of 3, and then was undetectable after four months. Testing of all samples stored at 40-42° C. was ceased after four months, see FIG. 10.

There was no real difference in the HA bio-activity for any of the H3N2 virus treatments through twelve months of storage at 2-7° C., 22-25° C. and 35-39° C.; the only exception being the loss of HA bio-activity to below the level of detection of the virus inactivated with IDU on the twelve month testing date. The HA bio-activity of the H3N2 virus inactivated with IDU appeared to be much more stable than the untreated or BEI inactivated H3N2 viruses through two months of storage at 40-42° C.

Testing was performed to determine whether the hemagglutinin protein from Swine Influenza Virus (SIV) isolates H1N2 and H3N2 is stabilized by the compound IDU using expanded inactivation conditions. Data from Phase I.B. demonstrated that 0.5% IDU was effective in the complete inactivation of SIV infectivity of both isolates (H1N2 and H3N2) after a 72 hour incubation at room temperature and did not affect the HA protein's ability to hemagglutinate red blood cells. However, the incubation of inactivated viruses at elevated temperatures resulted in different levels of HA bio-activity stability over time. The level of HA bio-activity stability was not the same for all the isolates tested.

Phase 3 Inactivation Studies Hemagglutination Bio-Activity Testing of the H3N2 Isolate Forced Degradation Samples Inactivated with 0.5% IDU Treatment of all Phase 3 samples with 0.5%, 1.0%, or 2.0% IDU for 24, 48, and 72 hours resulted in complete SIV infection inactivation (≤1.5 TCID$_{50}$/ml). No cytopathic effect was observed in indicator cells. As expected, there was a minimal cytotoxic effect due to the IDU. The SIV positive control (not inactivated) yielded a titer of 5.5 TCID$_{50}$/ml on the indicator cells.

The H3N2 SIV isolate was inactivated using 0.5% IDU at room temperature, 35-39° C. and 40-42° C. for 24, 48 and 72 hours. The H1N2 SIV isolate was inactivated using 0.5%, 1.0% and 2.0% IDU at room temperature, 35-39° C. and 40-42° C. for 24, 48 and 72 hours. Bulk preparations of each sample were placed at 2-7° C., 35-39° C. and 40-42° C. for the forced degradation assay. Samples were collected and tested for HA bio-activity on days 0, seven, fourteen, and twenty-one, and once monthly for six months.

The HA bib-activity was tested at time 0, day seven, day fourteen, day twenty-one, and once monthly for six months. All samples collected to date have been tested for HA bio-activity using cRBC. The positive control (H3N2 not-inactivated) had an HA bio-activity titer of 6 or 7 during the six months. The initial HA bio-activity was retained in all samples tested regardless of the incubation temperature or time of incubation used to inactivate the samples. The HA bio-activity of all H3N2 viruses stored at 2-7° C. retained an HA titer of 6 during the first month of incubation, then fluctuated between titers of 5 and 6 through six months, see FIG. 11. The HA bio-activity of all H3N2 viruses stored at 35-39° C. retained an HA titer of 6 during the first month of incubation, then fluctuated between titers of 4 and 5 through six months see FIG. 12. The HA bio-activity of all H3N2 viruses stored at 40-42° C. retained a titer of 6 for the first seven days then decreased to a titer of 3 after two months. The HA bio-activity of all H3N2 viruses fluctuated between titers of 2 and 4 through five months of incubation, then was not detected (titer <2) after six months, see FIG. 13.

There was no real loss of HA bio-activity for any of the H3N2 virus treatments stored at 2-7° C. through six months. All treatments of the H3N2 virus stored at 35-39° C. retained a HA bio-activity titer of 6 through one month, then dropped to a titer of 4 after six months. All treatments of the H3N2 virus stored at 40-42° C. retained HA bio-activity titers within 2-fold of each other throughout six months except at the four month testing date. After four months of storage at 40-42° C., there was a 3-fold difference in titer between the virus inactivated at 37° C. for 24 and 48 hours and the virus inactivated at 41° C. for 72 hours. However, all treatments stored at 40-42° C. returned to a titer of 3 after five months, then the HA bio-activity was not detected after six months.

Figure 14:
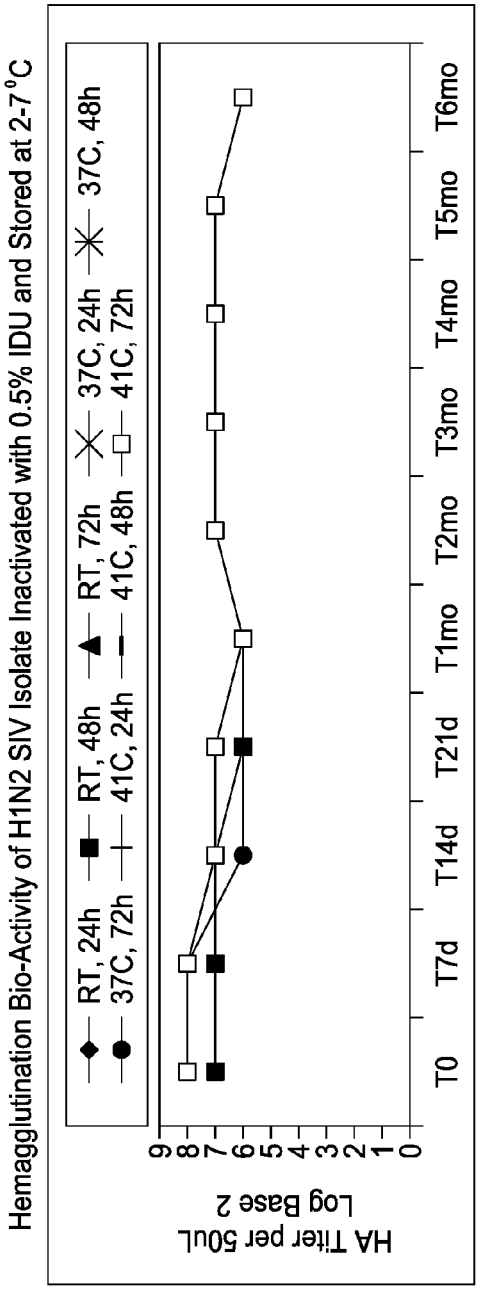

Phase 4 Hemagglutination Bio-Activity Testing of the H1N2 Isolate Forced Degradation Samples Inactivated with 0.5%, 1.0% and 2.0% IDU The HA bio-activity has been tested at time 0, days seven, fourteen twenty-one, and each month for six months. All samples collected to date have been tested for HA bio-activity using cRBC. The HA titer for the positive control (H1N2 not-inactivated) remained consistent at 7 or 8 during the six months. The incubation temperature, time of incubation, or concentration of IDU used to inactivate the samples did not affect the initial HA titer. The HA bio-activity of all H1N2 viruses inactivated with 0.5% IDU and stored at 2-7° C. fluctuated between titers of 6-8 through six months of incubation, see FIG. 14. The HA bio-activity of all H1N2 viruses inactivated with 0.5% IDU and stored at 35-39° C. fluctuated between titers of 7 and 8 through the first seven days, then fluctuated between titers of 5 and 7 through four months of incubation. The HA bio-activity of the H1N2 viruses fluctuated between titers of 4 and 5 after five months of incubation and then decreased to a titer of 4 after six months, see FIG. 15. The HA bio-activity of all H1N2 viruses inactivated with 0.5% IDU and stored at 40-42° C. fluctuated between a titer of 7 and 8 for the first seven days, then fluctuated between a titer of 5 and 6 through three months of incubation. After six months of incubation the HA bio-activity of all H1N2 viruses decreased to a titer of 2 or 3 see FIG. 16. The HA bio-activity of all H1N2 viruses inactivated with 1.0% IDU and stored at 2-7° C. started at a titer of 7 or 8 and fluctuated between titers of 6 and 7 through five months of incubation. After six months of incubation the HA bio-activity of all H1N2 viruses decreased to a titer of 6, see FIG. 17. The HA bio-activity of all H1N2 viruses inactivated with 1.0% IDU and stored at 35-39° C. started at titers of 7 or 8, then fluctuated between a titer of 5 and 7 through three months of incubation. After six months of incubation the HA bio-activity of all H1N2 viruses decreased to a titer of 4, see FIG. 18. The HA bio-activity of all H1N2 viruses inactivated with 1.0% IDU and stored at 40-42° C. started at titers of 7 or 8, then fluctuated between titers of 4 and 6 through three months of incubation. After six months of incubation the HA bio-activity of all H1N2 viruses inactivated at room temperature for 24 or 48 hours decreased to a titer of 1 and all remaining H1N2 viruses decreased to a titer of 2, see FIG. 19. The HA bio-activity of all H1N2 viruses inactivated with 2.0% IDU and stored at 2-7° C. fluctuated between titers of 5-7 through six months of incubation, see FIG. 20. The HA bio-activity of all H1N2 viruses inactivated with 2.0% IDU and stored at 35-39° C. started at a titer of 6 or 7, then fluctuated between titers of 4 or 6 through four months of incubation. After six months of incubation the HA bio-activity of all H1N2 viruses decreased to a titer of 3, see FIG. 21. The HA bio-activity of all H1N2 viruses inactivated with 2.0% IDU and stored at 40-42° C. decreased from a titer of 6 or 7 to titers of 3 and 4 after two months of incubation. The HA bio-activity of all H1N2 viruses returned to a titer of 5 after three months. After six months of incubation, the H1N2 viruses inactivated at room temperature (24, 48 or 72 hours) or at 37° C. for 24 hours decreased below the level of detection (titer of <2); the H1N2 viruses inactivated at 37° C. for 48 or 72 hours decreased to a titer of 1; and the H1N2 viruses inactivated at 41° C. (24, 48 or 72 hours) decreased to a titer of 2, see FIG. 22.

The H1N2 virus was inactivated using 0.5%, 1.0% and 2.0% IDU at various temperatures and incubation periods. Each inactivated preparation was placed at 2-7° C., 35-39° C. and 40-42° C. for storage for six months. The initial HA bio-activity of all H1N2 viruses inactivated with 0.5% and 1.0% IDU was slightly higher than the initial HA bio-activity for the H1N2 viruses inactivated with 2.0% IDU, average of 7.3 and 6.7, respectively. There did not appear to be an overt difference between the inactivation conditions regarding the stability of the HA bio-activity during incubations at the lower temperatures. However, there was a slight increase in the retention of HA bio-activity in the groups when incubations were performed at higher temperature. There was no real loss of HA bio-activity for any of the H1N2 viruses stored at 2-7° C.; the titer for all viruses after six months was within 2-fold of the original titer. The pattern of HA bio-activity, for all H1N2 viruses stored at 35-39° C. was similar; all viruses decreased 3 to 4-fold in titer after six months of storage. The pattern of HA bio-activity for all H1N2 viruses stored at 40-42° C. was also similar, but the stability of the HA bio-activity appeared to decrease slightly as the concentration of IDU used for inactivation increased.

All H1N1 isolate samples collected within the first fifteen months of storage were also tested using one lot of cRBCs. This testing was conducted to determine whether differences in HA titers were observed between each of the original testing dates (in which various lots of cRBCs were used) and using one lot of cells. Small differences were observed between the titers (within 2-fold) and are probably attributable to the natural variation of the assay. Samples of the untreated H1N1 virus collected at 3 and 3.5 months of storage at 40-42° C. had no detectable titer when originally tested (titer <2), but had titers of 8 and 16, respectively, when tested using one lot of cRBCs (Appendix II). It is possible that there was some degradation of virions in these samples that may have caused the number of HA subunits per particle to increase if all HA subunits disassociated from the virion. The H1N2 and H3N2 isolates were assayed through one year of storage at 2-7° C., 22-25° C., 35-39° C. and 40-42° C. and the stability of the IDU-treated samples compared to BEI-treated or untreated samples. The isolates were inactivated using IDU or BEI at room temperature for 72 hours. IDU did not appear to provide much stability of HA bio-activity of the H1N2 preparation used in this phase of the study. The IDU-treated H1N2 isolates had a lower amount of HA bio-activity at every-storage temperature throughout the 12 month period (FIGS. 3-6). This was not true for the H3N2 isolate. Although there was no real difference in HA bio-activity between any of the H3N2 isolate treatments at the 2-7° C., 22-25° C. or 35-59° C. storage temperatures, the IDU-treated isolate maintained a 3 to 5-fold higher HA bio-activity titer than the BEI-treated isolate at the 40-42° C. storage temperature (FIGS. 7-10). Therefore, it appears that the H3N2 isolate benefitted from treatment with IDU if stored at 40-42° C. The H1N2 and H3N2 isolates were also assayed through six months of storage at 2-7° C., 35-39° C. and 40-42° C.; however these samples were not compared to BEI or untreated isolates. Instead, various conditions of IDU-inactivation were compared. No real difference was observed between the HA bio-activity of the isolates inactivated using the various conditions; all conditions tested were within 2-fold of each other at each testing period (FIGS. 11-22). The H3N2 isolate behaved very similarly between this phase of the study (FIGS. 11-13) and the phase in which the isolate was inactivated only at room temperature for 72 hours (FIGS. 7-10). The HA bio-activity of the H1N2 isolates inactivated using 0.5% IDU appeared to be slightly more stable than the isolates inactivated with 1.0% or 2.0% IDU at the elevated temperatures (35-39° C. and 40-42° C.). This supports previous studies that suggested a range of 0.25% to 0.5% IDU was useful to inactivate virus and stabilize HA bio-activity. The H1N2 preparation used in this phase of the study (FIGS. 14-22) appeared to be much more stable than the preparation used in the earlier studies where the isolate was inactivated at room temperature for 72 hours (FIGS. 3-6); this was most evident especially at the higher temperatures. This may be because the H1N2 isolate used in this phase of the study was re-expanded and the new material had a 2-fold higher HA bio-activity titer than the previous material. The increased number of virions and the resulting change in the ratio of IDU to virus mass may have aided in its overall greater stability in this phase of the study. These results suggest that IDU is beneficial for stabilizing the HA bio-activity of the H1N1 and H3N2 isolates, compared to BEI-treatment, when stored at elevated temperatures. The H1N2 isolate also appeared to have benefitted from treatment with IDU, but not this was not consistent between two preparations of the virus. There is a greater amount of HA stability observed with the H1N2 isolate if the initial HA bio-activity is higher (at least 7), but the stabilization of this isolate at the higher initial titer was not compared to BEI-treatment. These results also support previous data suggesting that a concentration of 0.5% IDU is optimal for use in inactivating virus and stabilizing HA bio-activity.

Table 4 shows the titer data measured.

Phase I.A.b: Comparison of Hemagglutination Bio-Activity of all Forced Degradation Samples of the H1N1 Virus Using Multiple or One Chicken Red Blood Cell Lots

| Sample | | T = 0 | | T = 7 d | | T = 14 d | | T = 21 d | | T = 1 mo | |
|---|---|---|---|---|---|---|---|---|---|---|---|
| | | | | | | HA Bio-Activity Titer/50 ul | | | | | |
| Un- | 2-7° C. | 128 | 256 | 128 | 256 | 256 | 128 | 128 | 128 | 128 | 256 |
| treated | 22-25° C. | N/A | N/A | 128 | 256 | 256 | 256 | 128 | 128 | 128 | 256 |
| Control | 35-39° C. | N/A | N/A | 128 | 256 | 256 | 128 | 128 | 128 | 128 | 128 |
| Virus | 40-42° C. | N/A | N/A | 128 | 128 | 128 | 128 | 32 | 32 | 16 | 32 |
| BEI- | 2-7° C. | 256 | 256 | 128 | 256 | 256 | 128 | 128 | 128 | 128 | 256 |
| Treated | 22-25° C. | N/A | N/A | 128 | 128 | 256 | 128 | 128 | 128 | 128 | 256 |
| Virus | 35-39° C. | N/A | N/A | 128 | 128 | 128 | 128 | 64 | 128 | 64 | 128 |
| | 40-42° C. | N/A | N/A | 128 | 128 | 64 | 64 | 4 | 4 | <2 | 4 |
| IDU- | 2-7° C. | 256 | 256 | 128 | 128 | 256 | 256 | 128 | 128 | 128 | 256 |
| Treated | 22-25° C. | N/A | N/A | 128 | 256 | 256 | 128 | 128 | 128 | 128 | 128 |
| Virus | 35-39° C. | N/A | N/A | 256 | 256 | 256 | 128 | 128 | 128 | 128 | 128 |
| | 40-42° C. | N/A | N/A | 128 | 128 | 256 | 128 | 128 | 128 | 32 | 64 |
| Phase | | 1 | 2 | 1 | 2 | 1 | 2 | 1 | 2 | 1 | 2 |
| Positive Control | | 256[1] | 128* | 256[1] | 128* | 256[1] | 128* | 128[1] | 128* | 128[1] | 128* |

| Sample | | T = 3 mo | | T = 3.5 mo | | T = 6 mo | | T = 12 mo | | T = 12 mo | | T = 15 mo | |
|---|---|---|---|---|---|---|---|---|---|---|---|---|---|
| | | | | | | HA Bio-Activity Titer/50 ul | | | | | | | |
| Un- | 2-7° C. | 128 | 256 | 128 | 256 | 64 | 256 | 256 | 128 | 256 | 128 | 256 | |
| Treated | 22-25° C. | 128 | 256 | 128 | 256 | 64 | 128 | 256 | 128 | 256 | 64 | 64 | |
| Control | 35-39° C. | 4 | 16 | 4 | 8 | <2 | 16 | 4 | 8 | 4 | NT | NT | |
| Virus | 40-42° C. | <2 | 8 | <2 | 16 | NT | NT | NT | NT | NT | NT | NT | |
| BEI- | 2-7° C. | 128 | 128 | 128 | 128 | 64 | 128 | 128 | 128 | 256 | 128 | 256 | |
| treated | 22-25° C. | 128 | 128 | 128 | 256 | 16 | 32 | 16 | 64 | 64 | 8 | 16 | |
| virus | 35-39° C. | 64 | 128 | 64 | 64 | <2 | 4 | 2 | 4 | 4 | NT | NT | |
| | 40-42° C. | <2 | 4 | <2 | 4 | NT | NT | NT | NT | NT | NT | NT | |
| IDU- | 2-7° C. | 128 | 128 | 128 | 128 | 64 | 128 | 128 | 128 | 128 | 128 | 256 | |

-continued

| | | | | | | | | | | | | | |
|---|---|---|---|---|---|---|---|---|---|---|---|---|---|
| treated virus | 22-25° C. | 128 | 128 | 128 | 256 | 64 | 64 | 128 | 64 | 128 | 64 | 128 |
| | 35-39° C. | 32 | 64 | 16 | 32 | <2 | 4 | <2 | 4 | 2 | NT | NT |
| | 40-42° C. | <2 | 2 | <2 | 2 | NT | NT | NT | NT | NT | NT | NT |
| Testing Dates | | 1 | 2 | 1 | 2 | 1 | 1 | 2 | 1 | 2 | 1 | 2 |
| Positive Control | | 128[1] | 128* | 128[1] | 128* | 128[1] | NT | 128* | NT | 128* | 128[2] | 128* |

Figure 25:
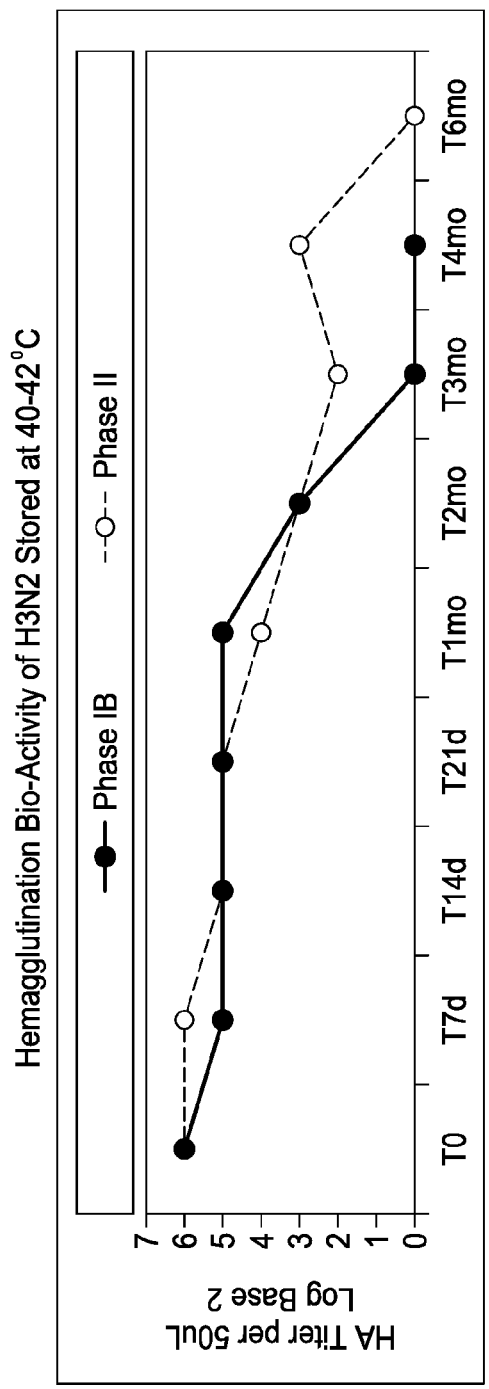
Figure 26:
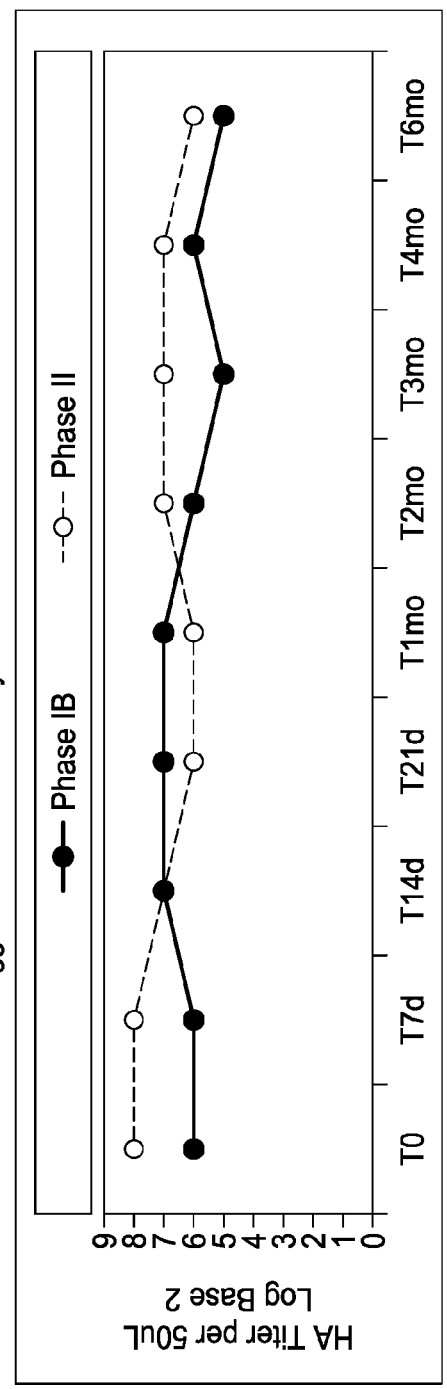

*Positive control virus tested once, 128 HA titer/50 ul
[1]H1N1 Iowa-73 isolate, not inactivated, used as positive control
[2]H1N2 SIV isolate, not inactivated, used as positive control
N/A = Not Applicable;
NT = Not Tested FIGS. 23 to 25 provide a comparison of the HA Bio-Activity for the H3N2 Virus Inactivated with 0.5% IDU for 72 Hours at Room Temperature between Phase I and Phase II. FIGS. 26 to 28 provide a comparison of the HA Bio-Activity for the H1N2 Virus Inactivated with 0.5% IDU for 72 Hours at Room Temperature between Phase I and Phase II Parts by weight as used herein refers to 100 parts by weight of the composition specifically referred to.

Any numerical values recited in the above application include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner. Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

What is claimed is:

1. A method comprising the steps of:
   a) providing a live swine flu virus having an infectious component and a plurality of surface antigens;
   b) contacting the live swine flu virus with a non-crosslinking chemical fixative that contains at least one urea-based formaldehyde donor agent having a molecular weight that is greater than 50 g/mol and less than 400 g/mol for de-activating the infectious component with the at least one urea-based formaldehyde donor agent, and for preserving at least a portion of the plurality of surface antigens sufficient to induce an immune response to form an antigen-treated deactivated virus composition such that a hemagglutination activity of the antigen-treated deactivated virus composition is retained for a period of at least 6 months; and
   c) storing and/or transporting the antigen-treated deactivated virus composition at ambient temperature from about 25° C. to about 37° C. without cold storage or transport.

2. The method of claim 1 wherein the live swine flu virus is grown in a tissue or in vitro cell culture.

3. The method of claim 1 wherein the at least one urea-based formaldehyde donor agent is selected from diazolidinyl urea (DU), imidazolidinyl urea (IDU), or a mixture thereof.

4. The method of claim 1 wherein the contacting step includes contacting the live swine flu virus with the at least one urea-based formaldehyde donor agent having a concentration of less than 1 w/v (grams per 100 ml total volume).

5. The method of claim 1 wherein the contacting step (b) occurs for a period of 24 to 72 hours.

6. The method of claim 1 wherein the contacting step (b) occurs at a temperature of 23° C. to 37° C.

7. The method of claim 1 wherein the method is free of any step of contacting the live swine flu virus or the antigen-treated deactivated virus composition with binary ethylene-imine, formaldehyde, formalin, phenol, 2-phenoxyethanol, thimerosal, bromo-ethylene-imine, ethyl methane sulfonate, nitrosoguanidine, fluorouracil, 5-azacytadine, or any combination thereof.

8. The method of claim 1 wherein the method includes a step of freeze-drying and re-hydrating the antigen-treated deactivated virus composition.

9. A method of preparing an immunogenic composition comprising the method of claim 1 which further comprises c) mixing a non-toxic effective amount of the antigen-treated deactivated virus composition with a pharmaceutically acceptable carrier to form a resulting composition for inducing an immune response in a subject to which the resulting composition is administered.

10. The method of claim 9 wherein the swine flu virus is provided in a live titer amount of $10^6$ to $10^{12} EID_{50}$ per milliliter of the resulting composition.

11. The method of claim 9 wherein the mixing step (c) occurs immediately following the contacting step (b).

12. A method for de-activating a live swine flu virus and retaining hemagglutination activity comprising the steps of:
   a) providing a live swine flu virus having an infectious component and a plurality of surface antigens;
   b) contacting the live swine flu virus with a urea-based formaldehyde donor agent having a molecular weight that is greater than 50 g/mol and less than 400 g/mol for de-activating the infectious component with the at least one urea-based formaldehyde donor agent, and for preserving at least a portion of the plurality of surface antigens to form an antigen-treated deactivated virus composition;
   c) transporting and/or storing the antigen-treated deactivated virus composition at ambient temperature from about 25° C. to about 37° C. without cold storage or transport; and
   d) performing a hemagglutination activity (HA) assay to confirm hemagglutination activity of a sample of the transported and/or stored antigen-treated deactivated virus composition.

13. The method of claim 1 wherein the contacting step (b) occurs for a period of 24 to 240 hours.

14. The method of claim 1 wherein the contacting step includes contacting the live swine flu virus with imidazolidinyl urea (IDU) having a concentration of from 0.0625% to 0.5% weight per volume (w/v).

15. The method of claim 1 wherein the live swine flu virus of step a) is free of any genetically modified or cloned virus.

* * * * *

UNITED STATES PATENT AND TRADEMARK OFFICE
CERTIFICATE OF CORRECTION

PATENT NO. : 9,956,281 B2
APPLICATION NO. : 14/112263
DATED : May 1, 2018
INVENTOR(S) : Wayne L. Ryan et al.

It is certified that error appears in the above-identified patent and that said Letters Patent is hereby corrected as shown below:

On the Title Page

Item (75), Line 2, "James A" should be -- James A. --.

Item (73), Line 1, "LaVista," should be -- La Vista, --.

In the Claims

At Column 22, Line 51, "5-azacytadine," should be -- 5-azacytidine, --.

Signed and Sealed this
Nineteenth Day of February, 2019

Andrei Iancu
*Director of the United States Patent and Trademark Office*